United States Patent [19]

Zhabilov et al.

[11] 4,415,553

[45] Nov. 15, 1983

[54] COMPOSITIONS, PROCESSES FOR THEIR PREPARATION AND METHOD FOR TREATMENT OF NEOPLASMS

[75] Inventors: Harry P. Zhabilov; Todor Y. Karavassileff, both of Razgrad, Bulgaria

[73] Assignee: DSO "Pharmachim", Sofia, Bulgaria

[21] Appl. No.: 127,343

[22] Filed: Mar. 5, 1980

Related U.S. Application Data

[63] Continuation-in-part of Ser. No. 861,072, Dec. 15, 1977, abandoned, which is a continuation-in-part of Ser. No. 577,719, May 15, 1975, abandoned, and Ser. No. 478,156, Jun. 10, 1974, abandoned, which is a continuation-in-part of Ser. No. 364,654, May 23, 1973, abandoned, which is a continuation of Ser. No. 51,094, Jan. 22, 1970, abandoned, which is a continuation-in-part of Ser. No. 865,539, May 19, 1969, abandoned, which is a continuation of Ser. No. 652,043, Jul. 10, 1967, abandoned, which is a continuation-in-part of Ser. No. 572,236, Aug. 15, 1966, abandoned, and Ser. No. 533,037, May 26, 1966, abandoned, said Ser. No. 572,236, is a continuation-in-part of Ser. No. 533,037, , abandoned.

[30] Foreign Application Priority Data

Aug. 6, 1973 [BG] Bulgaria ................................. 23841

[51] Int. Cl.$^3$ ..................... A61K 37/10; A61K 35/12; A61K 39/00; C12P 21/00; C12P 21/06; C12N 15/00; C12N 5/00
[52] U.S. Cl. ....................................... 424/95; 424/177; 424/180; 435/68; 435/69; 435/172; 435/240; 260/112.5 R; 260/112 R

[58] Field of Search ......................... 424/95, 177, 180; 260/112.5, 112; 435/68, 69, 172, 240

[56] References Cited

PUBLICATIONS

Matsubara, Chem. Abs., vol. 56, 1962, p. 2838g.
Irie, Int. J. Cancer, vol. 6, 1970, p. 304.
Irie, Int. J. Cancer, vol. 4, 1969, p. 150.
Irie, Cancer Res., vol. 31, 1971, p. 1682.

*Primary Examiner*—Anna P. Fagelson
*Attorney, Agent, or Firm*—E. Janet Berry

[57] ABSTRACT

The invention comprises preparations for the treatment of neoplasms, the methods of treatment of neoplasms using such preparations, and processes for preparing such preparations, including the step of selective enzymatic degradation of the nuclei of cancer cells.

The invention further comprises the method of treating patients suffering from neoplasms with immunomodulating agents obtained by isolating the genetically active components of cancer cell nuclei obtained from cancer tissue, subsequently recombining them by specific hybridization steps to prepare a vaccine therefrom, and intravenously, intraperitoneally and/or intramuscularly administering the resulting vaccine product to patients. The neoplastic tissue used may be obtained by surgical removal either from the diseased portion of the patient's body who suffers from the neoplasm or from another patient who suffers from the same or similar type and form of neoplasm as the patient to be treted by said method, or from tumors transplanted into animals or from virus-, chemically-, irradiation-caused tumors in animals or from spontaneous tumors in animals.

14 Claims, 2 Drawing Figures

METHOD OF PREPARATION

TO FIG. 1B

COMPOSITIONS, PROCESSES FOR THEIR PREPARATION AND METHOD FOR TREATMENT OF NEOPLASMS

This application is a continuation-in-part of copending application Ser. No. 861,072 filed Dec. 15, 1977, now abandoned. This application is in turn a continuation-in-part application of applications Ser. Nos. 478,156 and 577,719, respectively filed on June 10, 1974 now abandoned and May 15, 1975 now abandoned. Application Ser. No. 478,156 is a continuation-in-part of application Ser. No. 364,654, filed May 23, 1973, application Ser. No. 364,654, now abandoned, being a continuation application of application Ser. No. 5,094, filed Jan. 22, 1970 and now abandoned, the latter being a continuation-in-part application of Ser. No. 865,539, filed May 19, 1969, now abandoned, the latter being in turn a streamlined continuation application of application Ser. No. 652,043, filed July 10, 1967, now abandoned, the latter being in turn a continuation-in-part application of two applications, namely application Ser. No. 572,236, filed Aug. 15, 1966, now abandoned, and application Ser. No. 533,037, filed May 26, 1966, now abandoned, application Ser. No. 572,236 being a continuation-in-part application of application Ser. No. 533,037, filed May 26, 1966, now abandoned.

The invention relates broadly to compositions, methods for their preparation, and methods of treatment of neoplasms in mammals.

One objective of the invention is to provide processes for preparing antigenic materials from human or animal cancer cells which materials will produce an immunological reaction when injected into animals or humans having cancer.

Another objective is to provide processes for preparing antigenic materials for the treatment of cancer in humans or other animals in which the genetically active components of cancer cells are isolated and subsequently recombined by hybridization.

It is a further objective of this invention to provide methods by which the immunologically active components of both the DNA and RNA of cancer cell nuclei can be isolated.

It is also an objective of the invention to define the active histone fractions which contribute immunological activity to an antigenic material and to describe processes for their isolation and to provide a preferred process for the combining or bonding of these histones with DNA and RNA.

An important objective of the invention is to provide methods by which antigenic materials obtained from animal cancer tissues by the processes of this invention can be correlated with specific human cancers so that such animal-derived antigenic materials can be selected for producing immunoregulators which are effective for the treatment of specific human cancers.

A major objective of the invention is to provide methods by which new nucleoproteides with varying and specific antigenic properties can be produced from histone fractions, single-strand DNA, and active RNA isolated from animal cancer cell nuclei.

The works of the investigators Monot and Jacob deal with the problem of why certain types of cells divide in a controlled manner within the limits of a living organism, system or individual, whereas others (neoplastic cells) divide in an irregular pattern which cannot be controlled. Many factors indicate that the cause of the irregular pattern of cell division is due to a change in the genetic apparatus which is located in the nucleus of the cell.

The literature throughout the world discloses and describes attempts to treat neoplastic diseases by implanting subcutaneously carcinogenic tissue in patients. Similarly, there is disclosed and described the use of a suspension of previously killed cancer cells or the administration of serum obtained from an animal recipient into which a human tumor has been heterotransplanted. In addition there exist reports of the treatment of patients with serums obtained from spontaneously-cured patients having the same type of neoplasm. Furthermore, it is also known to treat patients with double strand DNA or proteins obtained from cancer cells.

All of the aforementioned attempts at treatment are of a complex nature. Generally and statistically speaking, continuous improvement in the condition of the patient by any one of the aforementioned treatments of the prior art does not exceed one percent.

REQUIREMENTS FOR ANTICANCER VACCINES

Immunological analyses (formation of antibodies in healthy rabbits after their injection with isolated normal nuclei) show a high titer (1:640) and cross reaction against a chromatin suspension from normal nuclei, within 25–50% limits, depending on the organs used as the chromatin source.

Initially, attempts were made to use cancer cell nuclei free from cytoplasm. However, impurities from cytoplasm were always found to be present on the surface of the nuclei prior to treatment with the proteolytic enzyme pepsin. Immunological analyses (formation of antibodies in healthy rabbits after their injection with isolated nuclei) showed only an average titer of up to 1:320. By cross-reaction against normal tissue nuclei, it was shown that these antibodies are directed to the external nuclear membrane.

The following facts were also determined:

1. Immunological analyses of the antibodies obtained against DNA, RNA and cancer nuclear proteins isolated from chromatin suspension showed that the crossed precipitation lines for cancer and normal tissues are caused by high molecular weight DNA (mol. wt. $9.8 \times 10^6$, for example) and by the nuclear protein fraction with a mol. wt. above 40,000.

2. Specific immunological precipitations against chromatin isolated from cancer cells were obtained: (1) with DNA with mol. wt. from $10^6$ to $2.6 \times 10^6$; (2) with RNA with a sedimentation constant between 2.8 and 8; (3) with complex DNA-RNA; (4) with the arginine-rich fraction of nuclear proteins.

3. In the immunological analyses from (2) above, some of the DNA and RNA samples gave crossed precipitation lines with antibodies against the complex of DNA-RNA. At the same time, the presence of arginine-rich histone in this complex gives a higher immunogenicity but the complex with histone becomes unstable if kept longer than 10 to 15 days.

4. Chromatin suspensions from tumor cells, which show the most marked crossed precipitations between the DNA-RNA complex and types of DNA and RNA which are chemically separated from the same type of tumor cells by methods which are described herein, possess demonstrated healing effects as a vaccine when applied to animals with the same types of tumors.

5. Chromatin suspensions obtained from normal tissues and which, by immunological analyses, show a strongly marked precipitation line equal to one given by the normal nuclear protein fraction with a mol. wt. above 40,000, give poor results when tested as a vaccine. Moreover, such a preparation leads to an intensification of above 50% in tumor growth.

Our discovery, as confirmed by immunological analyses, that there are specific structural DNA, RNA and protein parameters which are essential to the preparation of an immunogenic material useful for the treatment of cancer has led us to the following conclusions:

I. The nuclear protein fraction must have a mol. wt. below 40,000. (The arginine-rich protein described herein.)

II. The content of the DNA-RNA complex must have a titer above 1:500.

III. The DNA-RNA complex must be bonded to the arginine-rich nuclear fraction.

IV. The cancer cell nuclear membrane must be removed prior to any processing of DNA, RNA and proteins.

V. The single-strand DNA must have a mol. wt. of less than $1.5 \times 10^6$.

The use of the enzyme trypsin according to the invention leads to successful elimination of the above described nuclear protein fraction of molecular weight above 40,000.

Vaccines prepared from animal tumors according to the methods discussed herein have been found acceptable for both good reproducibility and standardization.

In the course of the early research and clinical studies, it was discovered that the processing of cancer cells with the enzyme pepsin, according to the invention, not only removes the nuclei cell membrane but also extracts a unique nuclear structural protein. Such a protein fraction cannot be isolated from normal cell nuclei. According to its structure, it is from the group of the globular proteins (it is precipitated by ammonium sulfate solution) with an alpha-configuration. Its molecular weight varies for different tumors within the limits of 9,500 to about 14,000. One molecule of the protein consists of 91 to 108 amino acids according to the tumor. The isoelectric point is between pH 4.8 and 5.3.

When immunoelectrophoresis is carried out with sera from healthy, non-cancer patients, this protein precipitates in the area of alpha-2-macroglobulins. In cancer patients, this reaction subsides with the progress of the disease and is essentially absent in patients at stages III and IV of the disease.

Accumulation of this protein in the cancer cells is directly related to the tumor growth. The amount of the protein increases per unit of cancer tissue until the cancer process develops within the limits of the organ. When the first cancer cells are invasive into the regional lymph nodes of the corresponding organ, the amount of the protein progressively decreases per unit of cancer tissue (gamma/gram) but does not entirely disappear until the death of the patient.

Animals which have spontaneous and transplanted tumors show a very low titer of anti-cancer antibodies normally present in healthy animals. After immunization with the protein isolated from cancer cells, this titer begins to increase again up to the 45th day from the beginning of the immunization at which time the titer reaches the level of healthy animals. The tumor growth is regressed and the tumor size is reduced to ¼–⅓ of that observed in the control animals. Microscopic analyses show the presence of cancer cells in the basic tumor and the disappearance of metastases in the lymph nodes. The cancer tissue is surrounded by connective tissue from the normal cells. The volume of cancer cells is decreased and an increased synthesis of basic proteins is observed in the nuclei.

If the immunization treatment described above is stopped for from 30 to 60 days after the 45th day, the titer of the antibodies against the nuclear protein begins to decrease and the tumor resumes its growth. However, the speed of the growth is reduced about 50% as compared to the speed of growth in control animals.

Experiments on animals have shown that, if the above described protein is incorporated into the anti-cancer vaccine, the healing effect increases by 2–4%. Most importantly there are no relapses in the animals cured, which were kept under observation until the natural end of their lives (up to 3 years for rats).

The protein, which is characteristic for cancer cell nuclei and which is isolated by enzyme treatment with pepsin, represents a large part of the molecule of the lysine-rich histone fraction (75–82%). It is very strongly connected with the DNA of the derepressed genetic centers; for this reason its extraction as a whole molecule from the normal cell nuclei is impossible.

Depending on the precusor cancer from which the lysine-rich protein is isolated, the lysine to arginine ratios in the protein will vary from about 4:1 to 6:1. Typical examples of these ratios in proteins from various tumors are 4.3:1, 5.1:1 and 6:1. Typical molecular weights of the lysine-rich fractions which have been used in vaccines are 12,400, 13,500, 13,800 and 14,700.

To obtain anticancer vaccine with high titer and maximum effectiveness, only the functionally changed nuclear components must be utilized. If the whole nuclear material is used, antibodies against the components which are identical for cancer and normal cells will also be formed in the body of the person under immunization. As a result, not only are both cancer and normal cells destroyed but the natural transplantation immunity is also suppressed; this leads to transformation of new groups of normal cells into cancer cells.

Immunological analysis by Ouchterlony's method (of rabbit hyperimmune serum obtained after immunization with the complex of the invention and serum obtained after immunization with a complex obtained from normal tissue) shows that the antibodies obtained are of a different type. There are no cross-precipitations. Another important difference between the two types of antibody response is that the titer obtained against the product from normal tissues is 4 to 8 times lower than that of the antibodies against the product from cancer cells.

The essence of the type of vaccine is that it is neither a total nucleoprotein, nor is it an individual component isolated from cancer nuclei, such as have been used by other workers in the field. The anticancer vaccine of the invention contains selected nuclear components which have been determined to be functionally different from those of normal cells.

Certain workers in the field have undertaken to prepare cancer vaccines or fractions for incorporation into cancer vaccines from cancer tissue. (For instance Black and coworkers described the precipitations obtained from "histone-like", acid-extractable proteins of cancer cells (not extracted or treated with pepsin) and (1) proteins in normal serums, specifically describing, for instance, non-specific protein-protein interactions between histones and a variety of proteins and (2) "specific" histones, which are antigen-antibody precipitations.) These latter precipitations are not antigenic compositions and are totally unlike the invention compositions; they are the result of the well-known reaction of antigens with antibodies produced by cancer patients after immunization with cancer histones. The antibodies of the reference are specific to the histone, not the cancer cells. The antigenic activity disclosed by Black and coworkers is limited to antihistone-antibody formations only.

Sarkar and coworkers prepared certain fractions which were made using the enzyme chymotrypsin. They show almost complete lack of activity at a pH of 7.6–8.

There are well-known and outstanding differences between the chemical actions of chymotrypsin and trypsin. It is known that chymotrypsin cleaves the —C—N—bond adjacent to the —C=O group of an aromatic amino acid, while trypsin cleaves the —C—N—bond adjacent to the —C=O group of a basic amino acid. Thus each of these enzymes cleaves the protein molecule only at specific points. The results obtained are manifested in that the products (fractions) are totally different and have different and various specific activities.

Miller and coworkers use DNase to liberate cationic histones from a DNA-histone complex in order to establish that the resulting products have germicidal action. The basic histones thus liberated are different from those of the investigators. They are only similar in that they are associated with DNA and are not part of the protein cover for DNA. They do show germicidal activity as would be expected from the known activity of many quaternary ammonium compounds. However, they have no effectiveness as vaccines or components of vaccines for cancer.

Further results from our theoretical and experimental work have confirmed other conclusions, as follows:

A. Single-strand DNA spontaneously present in the nuclei of cancer cells is present in considerably larger amounts than it is in normal cell nuclei.

B. Single-strand DNA has a several times higher immunogenicity than two-strand DNA.

ACTIVE COMPONENTS OF IMMUNOTHERAPEUTIC PRODUCTS

A theoretical rationale for the exceptional immunotherapeutic activity of the materials prepared by the invention derives from the inter-relationships between cancer-active s-DNA; cancer-active RNA; and the lysine-rich and arginine-rich basic histones which are responsible for the repression and derepression of genomes. It is to be understood that the invention is not dependent upon nor limited by the theoretical concepts presented below.

It is known that different histone fractions inhibit in different ways the matrix activity of DNA. The lysine-rich fraction acts as a matrix inhibitor, while the arginine-rich fraction conjugated with RNA-polymerase inhibits information RNA synthesis. We have found that the specific DNA repressor is localized in the cell nuclei and is bound to DNA in a nontranscribing sector through dihydrouridylic acid. One difference between tumor and normal tissues results from changes in functional interactions between the basic lysine-rich histones and DNA. The histone molecules are not firmly bound to certain areas of DNA; they can change their positions through changes in covalent bonding. These changes are associated with derepressed zones containing cancer-active DNA.

Experiments starting in 1967 to define more distinctly the interrelationships between DNA, RNA and the basic histones suggest that anticancer activity cannot be attained unless antibodies directed against definite nuclear structures defined by the cancer-active zones are produced in the patient by the introduction of antigens containing these cancer active zones.

Hybridization and denaturation experiments have demonstrated that the existence of a type of RNA which takes part in the process of DNA-matrix repression really exists and that this same RNA serves to indicate which of the two DNA chains must be transcribed by the information RNA. In the cancer process, a "cancer-active" RNA exists which specifies the transcription of a cancer-active strand of DNA which remains uncovered by an arginine-rich histone fraction. Thus, a difference in functional activity between normal and tumor tissues consists in the definite way in which conjugation and distribution take place between the nuclear components DNA, RNA and histones.

It has been found that all cancer tissues contain the cancer-active type of RNA. Most cancer tissues contain this active type in a major proportion to the normally occurring RNA, generally in a ratio of 8–9 to 1. Similarly, the cancer-active (or derepressed) strand of DNA present in cancer tissue is generally present in a ratio of about 1:1 to 2:1 to the normal, or non-cancer specific DNA. A method of measuring and isolating normal DNA and RNA in cancer cells involves their conjugation with embryonic DNA and RNA obtained from a healthy mammal.

It has been found that the ratio of the total amount of active DNA and RNA which is present in the cancer tissue to the total amount of normal DNA and RNA which is present defines the aggressiveness of the cancer. The higher the percentage of specific cancer genome that is present, the more aggressive is the cancer. It is important that the immunotherapeutic materials of the invention contain not only the cancer-active DNA and RNA fractions but that these components be present in approximately the ratio which exists in the cancer being treated.

An essential part of the invention is the presence in the immunotherapeutic product of single-strand, cancer-active DNA and the absence of any substantial amount of double-strand DNA. It is also important that the cancer-active DNA in the vaccine be bound directly to the lysine-rich histone which is usually attached to the derepressed DNA. It has been found that the lysine-rich fraction which is bound to the derepressed DNA is easily extracted with proteolytic enzymes. Repressed DNA can subsequently be removed from the residual deaggregated material by denaturation. Subsequent hybridization then binds the lysine-rich fraction to the cancer-active DNA that was conjugated to RNA bound to an arginine-rich histone.

The above can be achieved by first isolating the cancer-active DNA, the cancer-active RNA, two lysine-rich and arginine-rich fractions and reconstructing them into a new nucleoproteide by selective recombination/hybridization steps. It is important to follow this procedure, especially so if the ratio of normal RNA to cancer-active RNA in the cancer cell is relatively high. It is also preferred to hybridize the lysine-rich fraction with the DNA-RNA hybrid prior to hybridization with the arginine-rich histone fraction.

In non-catalytic hybridization or complexing of lysine-rich histone with a DNA-RNA hybrid or with a DNA-RNA arginine-rich histone complex, the lysine-rich histone is combined with the DNA in a yield of only 60-65%. Catalysis and binding with streptomycin or streptomycin-cysteine increases the yield to 80-85% and increases the stability and activity of the immunotherapeutic material.

In connection with the activity and the effectiveness of the vaccines of the invention, the term vaccine has been used to describe the immunogenic activity which the new products possess. In this invention and in the practice of the processes and use of the invention vaccine compositions, it is to be understood that broader concepts and all possible immune activities are included.

In the past vaccines were considered as agents useful primarily for the stimulation of antibodies.

While the specific activities and in vivo functions of the hereindescribed vaccines are not entirely known, it is believed that they may be immunoactive within a broad range of biological activities which are involved in or related to the whole subject of the cancer patient's defense against the cancer cells. It may well be, for example, that they function as immunomodulating agents and thereby be stimulators of cell-mediated immunity to produce an appropriate response. They may function as immunoactive molecules and thereby produce inhibition of cell medicated immune responses. The vaccines may also function as immunopharmacological agents and thereby stimulate the production of antibodies which are active against the cancer. They may also act as immunoregulators. They may also induce interferon formation.

It is contemplated that these vaccines may, in fact, perform one, several or all of these functions and possibly, some functions at present unknown or little understood.

ANIMAL TUMORS AS MATERIAL SOURCE FOR TREATMENT OF HUMAN AND ANIMAL TUMORS

It has been found that cancer-active DNA and cancer-type RNA of animal tumors correspond functionally with human tumors and that their relative functionality can be quantitatively measured by DNA and RNA hybridization experiments.

The total cancer genome present in the human tumor can be determined by hybridization of denaturated DNA from the human tumor with DNA from normal calf thymus gland and, separately, RNA from the human tumor with denatured RNA from normal calf thymus gland. The total % bonding of these hybridizations represents the total non-specific cancer genome present.

Further extension of such hybridization studies to include hybridizations of d-DNA and RNA from animal corners with d-DNA and RNA from human cancers provide data essential to establishing the required ratios of s-DNA to RNA (from animal cancers) which must be present in immunotherapeutic products used for treatment of human cancer patients. The hybridization data are also essential to selection of the animal bearer and tumor which will be effective and safe for the preparation of a vaccine for a specific human tumor.

Animal and human tumors used for the hybridization studies referred to above are summarized in Table 1 below. The use of the Ref. Nos. of Table 1 are continued in Tables 2-9 for proper identification of specific tumor data.

TABLE 1

Summary of Human and Animal Tumors Used for Vaccine Composition Studies

| Ref. No. | Human Tumor | Animal Tumor and Source |
|---|---|---|
| 1 | Intestine | Yoshida in Rats |
| 2 | Hodgkin's | Squamous Cell in Hamsters |
| 3 | Lung | Guerins Carcinoma in Rats |
| 4 | Stomach | Yoshida in Rats |
| 5 | Breast | Yoshida in Rats |
| 6 | Throat | Guerin Carcinoma in Rats |
| 7 | Liver | Guerin Carcinoma in Rats |

Results of such determinations are given in Table 2 below, and Tables 3-6.

TABLE 2

% Hybridization with Normal Calf Tissue (d-DNA with RNA)

| Ref. No. | Human Cancer d-DNA or RNA | Thymus Gland d-DNA or RNA | % of Non-specific Genome | Specific Genome |
|---|---|---|---|---|
| 1 | Intestine | 3 | 42 | 45 | 55 |
| 2 | Hodgkin's | 44 | 11 | 55 | 45 |
| 3 | Lung | 19 | 13 | 32 | 68 |
| 4 | Stomach | 23 | 0 | 23 | 77 |
| 5 | Breast | 32 | 2 | 34 | 66 |
| 6 | Throat | 21 | 9 | 30 | 70 |
| 7 | Liver | 2 | 40 | 42 | 58 |

The relatively low percentages of the DNA hybridizations with RNA from intestinal and liver cancers correlate with their conception as RNA virus-induced cancers. The DNA virus-induced cancers give relatively low percentages of hybridizations with normal calf thymus RNA. The most effective treatment of RNA virus-induced cancers is obtained when the amount of RNA in the hybridized nucleoproteide vaccine is greater than the amount of DNA. In the treatment of DNA virus-induced cancers, the most effective vaccines contain more DNA than RNA.

The differences between DNA cancers and RNA cancers can also be seen in the differences in the degree of hybridization between animal cancer DNA and human cancer DNA and the degree of hybridization between animal cancer RNA and human cancer RNA, as set forth in Table 3 below.

TABLE 3

Hybridization of DNA and RNA from Animal Cancers with DNA and RNA from Human Cancers

| RNA or Denatured DNA from Cancer of the: | Percent Hybridization of Animal Cancer | |
|---|---|---|
| | d-DNA | RNA |
| 1. Intestine | 15.7 | 59 |
| 2. Hodgkin's | 68.3 | 6 |
| 3. Lung | 65 | 25 |
| 4. Stomach | 61 | 11 |
| 5. Breast | 68.3 | 18 |
| 6. Throat | 44 | 23 |
| 7. Liver | 7.3 | 58 |

The percent hybridizations in Table 3 above are the mean hybridization values from experiments with several transplantable animal cancers. The ratios of the percent hybridization of d-DNA to the percent hybridization of RNA are proportional to the ratios of s-DNA and RNA which should be present in the products prepared by the hybridization process of the invention. It has been shown, however, that little advantage in therapeutic effectiveness results from use of s-DNA to RNA greater than 5:1 or less than 1:5.

The animal tumor which will be most effective as a raw material source is that tumor whose RNA gives the highest percentage of hybridization with RNA of the human tumor to be treated. If this RNA hybridization is essentially equivalent for several tumors, then that tumor which gives the highest percentage of hybridization between denatured DNA from the animal tumor and denatured DNA from the human tumor is preferred. Table 4 below illustrates this.

age value of the three animal tumors was used as a guide to establish this ratio for the vaccine.

The use as raw material source for the vaccine of a type of animal cancer whose DNA and RNA activities differ appreciably from those of the human tumor can cause host rejection of the vaccine or initiate a new type of tumor growth in the patient. For RNA induced cancers, the percent hybridization of $RNA_c^h$ with $RNA_c^a$ should approximate the percent hybridization of $RNA_c^h$ with the d-DNA of the human cancer. For DNA induced cancers, the percent hybridization of $DNA_c^a$ with $d\text{-}DNA_c^h$ should approximate the percent hybridization of $RNA_c^h$ with the d-DNA of the human cancer. The following table shows this correlation.

TABLE 4

Hybridization with Animal Tumors; Animal Cancer Used; % Hybridization

| Denatured DNA (or RNA) from Cancer of | Yoshida in Rats | | Guerin Carcinoma in Rats | | Squamous Cell in Hamsters | |
|---|---|---|---|---|---|---|
| | d-DNA | RNA | d-DNA | RNA | d-DNA | RNA |
| 1. Intestine | 19 | 62* | 21 | 49 | 7 | 66 |
| 2. Hodgkin's | 66 | 8 | 88 | 2 | 51 | 8* |
| 3. Lung | 59 | 29* | 63 | 33* | 73 | 12 |
| 4. Stomach | 68 | 11* | 71 | 11* | 44 | 11 |
| 5. Breast | 66 | 22* | 70 | 20 | 69 | 11 |
| 6. Throat | 43 | 21 | 40 | 40* | 49 | 7 |
| 7. Liver | 3 | 80* | 0 | 54* | 19 | 39 |

*Designates animal tumor suitable for vaccine

Other animal tumors which have been shown to be effective raw material sources for this method are shown above.

It has also been shown that animal tumors whose d-DNA combines with the d-DNA of the human tumor in a higher percentage than the total cancer genome which is present in the human cancer (Table 2) are not preferred materials for preparation of vaccines against that human tumor. Thus, Guerin carcinoma and squamous cell (Table 4) are not used to prepare vaccines for treatment of fibrous cancer of the breast, and Yoshida and Guerin's carcinoma are not used to prepare vaccine for treatment of Hodgkin's cancer.

The optimum DNA to RNA ratios in the vaccines prepared from transplantable tumors will vary somewhat from the average values calculated from the data of Table 3, since the specific DNA and RNA reactivities of the animal tumor used will vary slightly from the average values used in Table 3. This is shown in Table 5.

TABLE 5

Weight Ratios of DNA to RNA in Effective Vaccine Compositions for Treatment of Human Tumors, Ref. Nos. 1–7 of Table 1

| | Optimum Ratios Calculated from Hybridization Experiments | | Actual Ratio in Vaccines, (Table 8 below) |
|---|---|---|---|
| Ref. No. | Average Value 3-Animal Tumors | Ratio Using Specific Tumor | |
| 1 | 1:3.76 | 1:3.27 | 1:2.5 |
| 2 | 1:0.09 | 1:0.09 | 1:0.16 |
| 3 | 1:0.38 | 1:0.52 | 1:0.53 |
| 4 | 1:0.18 | 1:0.16 | 1:0.16 |
| 5 | 1:0.26 | 1:0.33 | 1:0.33 |
| 6 | 1:0.52 | 1:1 | 1:1 |
| 7 | 1:7.9 | — | 1:5.3 |

The negligible reaction of $d\text{-}DNA_c^a$ with the d-DNA of the human liver cancer precluded calculation of the optimum DNA to RNA ratio in the vaccine. The aver-

TABLE 6

Reactivity Relationship of Human Cancer with Animal Cancers Used for Vaccine Preparations

| | % Hybridization | % Hybridization | |
|---|---|---|---|
| Ref. No. | $RNA_c^h$ with $d\text{-}DNA_c^h$ | $RNA_c^a$ with $RNA_c^h$ | $d\text{-}DNA_c^a$ with $d\text{-}DNA_c^h$ |
| 1 | 55 | 62 | — |
| 2 | 54 | — | 51 |
| 3 | 73 | — | 63 |
| 4 | 76 | — | 68 |
| 5 | 69 | — | 66 |
| 6 | 66 | — | 40 |
| 7 | 65 | 54 | — |

Using the above concepts and determined parameters, vaccines having the following compositions were prepared. All preparations showed effective anti-cancer activity (Tables 7–9).

TABLE 7

Properties of s-DNA and RNA Used for Vaccines

| Ref. No. | Mol. Wt. s-DNA | $S_{20}$ RNA |
|---|---|---|
| 1 | $1.16 \times 10^6$ | 4.2S |
| 2 | $8.3 \times 10^5$ | 4.8S |
| 3 | $9.08 \times 10^5$ | 5.2S |
| 4 | $6.03 \times 10^5$ | 5.1S |
| 5 | $7.04 \times 10^5$ | 6.0S |
| 6 | $4.29 \times 10^5$ | 4.2S |
| 7 | (*) | 4.8S |

(*) s-DNA from normal calf thymus used to complete bonding of nucleoproteide in absence of reaction of Guerin's Carcinoma s-DNA with liver cancer s-DNA.

TABLE 8

Composition of Nucleoproteide Complexes for Vaccines

| Ref. No. | Wt. Ratios of Components of Nucleoproteides | | | |
|---|---|---|---|---|
| | DNA | to RNA | to LRF | to ARF |
| 1 | 1.0 | 2.5 | 2.75 | 4.0 |
| 2 | 1.0 | 0.16 | 2.34 | 0.53 |
| 3 | 1.0 | 0.53 | 2.75 | 1.34 |

TABLE 8-continued

| | Composition of Nucleoproteide Complexes for Vaccines | | | |
|---|---|---|---|---|
| Ref. | Wt. Ratios of Components of Nucleoproteides | | | |
| No. | DNA | to RNA | to LRF | to ARF |
| 4 | 1.0 | 0.16 | 1.44 | 0.50 |
| 5 | 1.0 | 0.33 | 1.88 | 0.83 |
| 6 | 1.0 | 1.0 | 2.36 | 2.13 |
| 7 | 1.0 | 5.3 | 2.22 | 8.3 |

TABLE 9

| | Composition of Vaccines of Nucleoproteide Components | | | |
|---|---|---|---|---|
| Ref. | Total Gamma per ml Vaccine | | | |
| No. | s-DNA | RNA | LRF | ARF |
| 1 | 540 | 1350 | 1485 | 2160 |
| 2 | 510 | 80 | 1191 | 271 |
| 3 | 582 | 306 | 1600 | 777 |
| 4 | 679 | 110 | 980 | 338 |
| 5 | 640 | 213 | 1200 | 528 |
| 6 | 725 | 728 | 1711 | 1571 |
| 7 | 180 | 950 | 400 | 1493 |

From the above studies and results of clinical trials, it has been shown that the ratio of total protein to total nucleic acids in a vaccine should be less than 3:1 and preferably less than 2.5:1. The ARF to DNA ratio in the vaccines for DNA dominant cancers should be below 2:1 and preferably below 1.5:1 to assure maximum effectiveness and absence of cancer recidivs.

TABLE 10

Specific Examples of Immunotherapeutic Compositions

A. Preparation used in breast adenocarcinoma.
  s-DNA 576 microgr/ml    mol. wt. 0.9 × 10⁶
  RNA 456 microgr/ml      sed. const. 4.8S
  Protein 723 microgr/ml  mol. wt. 14,000 - 2 fractions
  Lysine:arginine ratio in Fraction A-1 4.3:1; mol. wt. 13,800
  Lysine:arginine ratio in Fraction F-1 0.6; mol. wt. 10,800
  Ratio of Fraction A-1 to Fraction F-1 is 3 to 1.
B. Preparation used in myeloid leukemia.
  s-DNA 466 microgr/ml    mol. wt. 1.4 × 10⁶
  RNA 547 microgr/ml      sed. const. 8S
  Protein 700 microgr/ml  mol. wt. 13,000 - 2 fractions
  Lysine:arginine ratio in Fraction A-1 5.1:1; mol. wt. 12,400
  Lysine:arginine ratio in Fraction F-1 0.53; mol. wt. 11,200
  Ratio of Fraction A-1 to Fraction F-1 is 3.2 to 1.
C. Preparation used in colon adenocarcinoma.
  DNA 639 microgr/ml      mol. wt. 2.0 × 10⁶
  RNA 463 microgr/ml      sed. const. 8S
  Protein 675 microgr/ml  mol. wt. 15,000 - 2 fractions
  Lysine:arginine ratio in Fraction A-1 6:1; mol. wt. 13,500
  Lysine:arginine ratio in Fraction F-1 0.43; mol. wt. 11,900
  Ratio of Fraction A-1 to Fraction F-1 is 1 to 3.3.
D. Preparation used in lymphogranulomatosis.
  DNA 612 microgr/ml      mol. wt. 1.8 × 10⁶
  RNA 508 microgr/ml      sed. const. 8.0S
  Protein 766 microgr/ml  mol. wt. 16,000 - 2 fractions
  Lysine:arginine ratio in Fraction A-1 5.4:1; mol. wt. 14,700
  Lysine:arginine ratio in Fraction F-1 0.6; mol. wt. 12,800
  Ratio of Fraction A-1 to Fraction F-1 is 4 to 1.
  The ratios of lysine to arginine and Fraction A-1 to Fraction F-1 above are given as weight ratios.
E. Vaccine Compositions used in Clinical Tests (Table 15) (content in gamma/ml. vaccine)

| Patient | s-DNA | RNA | LRF | ARF |
|---|---|---|---|---|
| Lung Carcinoma | | | | |
| G. B. | 1,200 | 640 | 2,240 | 1,340 |
| Breast Cancer | | | | |
| E. M. | 740 | 575 | 1,184 | 418 |
| I. C. | 893 | 710 | 1,428 | 476 |
| Lymphogranulomatosis | | | | |
| D. P. | 800 | 638 | 1,200 | 628 |
| Lymphosarcoma | | | | |
| S. B. | 360 | 900 | 718 | 630 |
| Stomach Adenocarcinoma | | | | |
| I. K. | 1,203 | 387 | 2,021 | 690 |

The therapeutic compositions which are optionally effective in the treatment of neoplastic diseases in mammals contain DNA, RNA and histones with properties and amounts relative to each other within about the following ranges:

A. Single-strand DNA—Molecular weight, $0.5 \times 10^6$ to about $1.5 \times 10^6$
B. RNA sedimentation constant—4S to 8S
C. Lysine rich histone Fraction A-1 (LRF):
  Molecular weight: 12,000 to 14,000
  Lysine to arginine mole ratio: 4:1 to 6:1
  DNA to LRF weight ratio: 0.5:1 to 4:1
D. Arginine rich histone fraction (ARF):
  Molecular weight: 10,500 to 13,000
  Lysine to arginine mole ratio 0.3:1 to 0.7:1
  RNA to ARF weight ratio: 0.8:1 to 3.5:1
E. LRF to ARF weight ratio: 3:1 to 1:4
F. DNA to RNA weight ratio: 0.3:1 to 3:1

Table 11 below sets forth additional relationships between various types and locations of human cancers and the types of cancer in animal hosts which can be used as sources for preparation of effective therapeutic compositions. These relationships have been established for use in preparing the compositions of the invention.

TABLE 11

| Animal Tumors Used for Human Tumor Treatment | |
|---|---|
| Experimental tumor | Human Cancer Disease Treated |
| 1. Friend Virus Leukemia C57B mice | Acute Myelogenic Leukemia |
| 2. Lymphoid Leukemia L-1210-Swiss Mice | Lymphogranulomatosis |
| 3. Yoshida's Sarcoma - Long Evans rats | Solid Scirrhous Carcinoma, Breast, Bone, Lung, and Stomach Cancers |
| 4. Novikov - Hepatoma - Long Evans rats | Primary Hepatocarcinoma |
| 5. Guerin's Carcinoma - Wiser rats | Adenocarcinomas, lung, liver, Throat and Pancreas Cancers |
| 6. Spontaneous mammary gland carcinoma - C3H/B mice | Mammary gland carcinoma |
| 7. Adenocarcinoma - Randombred hamsters | Adenocarcinoma of Stomach |
| 8. H-Sarcoma - Randombred hamsters | Cervix, Uterus, Brain Cancers and Carcinoma of Rectum |
| 9. Squamous cell carcinoma - hamsters | Ovarian (solid type) and Tongue Cancers |
| 10. Melanoma - hamsters | Melanoma and Gall Bladder Cancers |

GENERAL DESCRIPTION AND DISCUSSION OF THE PROCESS

A number of processes have been developed to prepare the highly active antigen complexes for use in cancer therapy. They are:

Process 1. Stepwise enzymatic degradations of nuclei from cancer cells with temperature denaturation of DNA therein.

Process 2. Enzymatic separation of lysine rich histone from nuclei of cancer cells, enzymatic removal of high molecular weight proteins, denaturation of the DNA contained in the product remaining therefrom to remove a single-strand DNA, and complexing of the lysine-rich fraction with the remaining single-strand DNA still bonded to RNA and arginine-rich histones.

Process 3. Degradation of the nuclei obtained from cancer cells with isolation of DNA, RNA and histone proteins therefrom and subsequent recombination/hybridization of the DNA, RNA and histone proteins into a new nucleo-proteide.

The first process is described and claimed in copending, continuation-in-part application Ser. No. 946,010. The second process is described and claimed in a copending continuation-in-part application filed simultaneously herewith.

The third process described herein yields nucleoproteide complexes which contain the genetically active single-stranded DNA of cancer cells combined with RNA, arginine-rich histone and a lysine-rich histone fraction that was attached to the active single-strand DNA in the original cancer cell and which are the subject matter compositions of this invention.

The products obtained for all three above outlined processes have therapeutic value. They differ principally in the amount and kind of the active cancer genomes which they contain, with the products from the third process containing the more active genomes which are present only in the highest concentration. The RNA components in the products obtained from the three processes above vary in their sedimentation constant as follows: Process 1, RNA=12S to 18S; Process 2, RNA=4S to 12S; and Process 3, RNA=2.8S to 8S. The ratios of DNA to RNA also vary in the products obtained from the three processesss. With process 2 the ratio of DNA to RNA is generally in the range of 0.75:1 to 1.5:1. Process 3 gives products with DNA to RNA ratios generally in the range of 5:1 to 1:5, as determined and specified by the type of cancer being treated.

The Japanese author, R. F. Irie, has obtained a product from cancer cells whose composition resembles the one obtained by us in the period 1963–1966, as described in parent application Ser. No. 624,708, and coincides in about 70–80 percent of its structure with the compositions obtained by the preferred process hereof. (Irie, R. F., Kataoka, T., Mitsui, H., Intern. J. Cancer, 6,304, 1970; Irie, R. F., Nishioka, T., Tachibana, T., Takeuchi, S., Intern. J. Cancer, 4, 150, 1969; and Irie, R. F., Can. Res., 31,11,1682, 1971). In our laboratory, the method of Irie has given products which show similar therapeutic results with those we have obtained in the treatment of experimental animal tumors using the compositions of our original method of preparation.

Improved control of the composition of the active nucleoproteide resulting in consistent high levels of anticancer activity is achieved with the process of this invention. The process also offers the opportunity to prepare nucleoproteides of highly specific activity by varying the source of the starting material for the preparation of one or more of the four components of the nucleoproteide.

An outline of the principal steps of the process above is as follows:

1. Separation under sterile conditions of cancer tissue obtained in the course of surgical intervention or from animals as outlined in the four sources listed hereinabove.

2. Cutting of the material in small pieces and removal of the normal tissue, the blood vessels and the necrotic parts.

3. Homogenization of the material in a saline or saccharose solution.

4. Separation of the cancer cell nuclei by centrifugation and treatment with detergents by one of the three methods: Choveau's method, Rev. Franc. Etudes Clin. Biol., 3,503, (1958); Stollar's method, J. Immunol., 103,4,804, (1969); Busch's method, Bioch., 8,6,2636, (1969).

5. Isolation of nuclear DNA from the nuclei by means of one of the following methods: Kirby's method, Bioch. J., 66,405 (1958); Gaito's method, Molecular Psychobiology, Ch. Thomas Publ. (1966); Hunter's method, J. Gen. Virol., 1,1,115, (1967).

6. Isolation of nuclear RNA from the nuclei by means of one of the following methods: Kumura's method, Biochem. Biophys. Acta., 37,373, (1962); Georgiev's method, Biochimia, 27,805, (1962); Method of Kidson Kirby, J. Mol. Biol., 7312, (1963).

7. Isolation of nuclear proteins by one of the following methods: Method of Busch-Grogan, Can. Res., 26,775, (1966); John's method, Biochem. J., 105,611 (1967); Bonner's method, Bioch., 8,8,3214, (1969).

8. Temperature denaturing of the isolated DNA and cleaning in accord with the method of: Albertson, Biochem. Biophys, Acta, 103-1, (1965).

9. Chromatographic dissociation of nuclear protein on CM-cellulose by pH-gradient (such dissociation is described by many authors).

10. Separation of acid soluble lysine-rich histones by enzymatic deaggregation of cell nuclei.

11. Isolation of DNA and RNA from the thymus of a calf or any other mammal, according to the aforesaid description Steps 5 and 6, with denaturing of the isolated DNA.

12. Hybridization between the denatured DNA isolated from cancer tissue and the nuclear RNA isolated from the calf thymus, and separation of the cancer-active DNA which is not bonded with RNA. Hybridization method of Nygaard-Hall, J. Mol. Biol., 9,125, (1964).

13. Hybridization between the denatured DNA isolated from the calf thymus and RNA isolated from cancer tissue, and separation of the cancer-active RNA which is not bonded with the DNA.

14. Hybridization of the non-bonded DNA from the previous hybridization of cancer-active DNA with the non-bonded RNA from the previous hybridization of cancer-active RNA and isolation of the hybrid DNA-RNA complex.

15. Binding or complexing the hybrid DNA-RNA complex with two histone fractions in a step-wise sequence in which the lysine-rich histone is the first fraction reacted.

16. Salification of the newly formed complex DNA-RNA protein fractions by gradual increase of the saline concentration of the solution and twofold washing of the precipitate formed.

17. Dissolving of the precipitate in an appropriate water-saline medium (for example, 0.14 M sodium chloride containing 1 percent polyvinylpyrrolidone and 0.014 M potassium citrate).

In the steps outlined above, Steps 10 through 15 form the basis of the invention process for producing varied compositions having a high level of therapeutic activity against cancer. We have found that compositions with only slightly decreased activity can be prepared by hybridization using cancer RNA without isolating the specific cancer-active RNA type from the normal RNA type which is present, provided the ratio of the active RNA to the more normal RNA is above about 6:1 to 7:1. When the ratio of the normal RNA to cancer RNA is relatively high, as in carcinoma of the large intestine (ratio of 1:1.5) and in cancer of the liver (ratio of about 1:1.2), it is preferred to isolate the specific cancer active RNA by hybridization of the normal RNA type with calf thymus DNA.

All the processes described above are performed under sterile conditions and in the temperature range between 0° C. and 6° and preferably about 4° C. with the exception of the DNA denaturation and the hybridization steps which require temperatures of 10° C. up to 100° C.

Sources of raw material for preparation of the vaccines include cancer tissues from both humans and animals. Essentially all animal tumors are useful raw materials.

All variations of Yoshida's carcinoma tissue, melanoma tissue obtained from hamsters, Rhabdomyasarcoma tissue obtained from hamsters, squamous-cell carcinoma tissue obtained from hamsters, and combinations thereof have been found to have particularly broad utility in preparing compositions for treatment. Suitable animals, which may be used for these purposes include mice, rats, rabbits, guinea pigs and the like.

GENERAL COMMENTS AND NOTATIONS

DNA is double stranded DNA.
d-DNA is temperatuare denatured DNA with both single strands present.
s-$DNA_n$ is one single-strand DNA from normal tissues.
s-$DNA_c$ is one single-strand DNA from cancer tissues. Superscripts h and a (human and animal) designate source of tumor.
Thus, $RNA_c{}^a$ is RNA from animal cancer tissue.
$DNA_c{}^h$ is DNA from human cancer tissue.
PVS is polyvinylsulfate.
EDTA is ethylenediaminetetraacetate, di-sodium salt.

It is to be understood that throughout this application in both the description, examples and claims all percentages referred to are percentages by weight unless otherwise specified.

The preparation of the lysine-rich nuclear histones is effected by means of the action of the enzyme pepsin upon the pure nuclei of cancer cells in a pH range of 2.8–4. Depending on the time and temperature used, papain is also effective in a pH range of 3.4–7.6. With either enzyme the use of lower pH's and higher temperatures reduces the time required for the reaction. The action of the papain is essentially the same under the varying reaction conditions. The use of papain is especially effective for recovering the histone fractions from nuclear membranes. Suitable time-temperature conditions for the use of papain vary from 4° C. for 18 hours to 36° C. for about 6 hours at a pH of 7. Use of lower pH's, such as 3.6, reduces the time required for papain treatment at 4° C. to about 10 hours.

"DETAILED DESCRIPTION OF PROCESS"

HYBRIDIZATION OF BIOLOGICALLY TRANSFORMALLY ACTIVE DNA AND RNA, WITH ANTIGENIC HISTONE FRACTIONS

Pure cancer cell nuclei are divided into four parts, from which four distinct products are obtained. One part is used to obtain a lysine rich histone by enzymatic degradation of the nuclei with the enzyme pepsin. The remaining three parts of the sediments used to obtain an arginine-rich histone fraction, a cancer-active denatured DNA fraction, and a cancer-active RNA fraction. These three fractions together with the lysine-rich histone are reconstituted in sequential hybridization steps to yield the synthetic nucleoproteide of the invention.

Figure 1A:
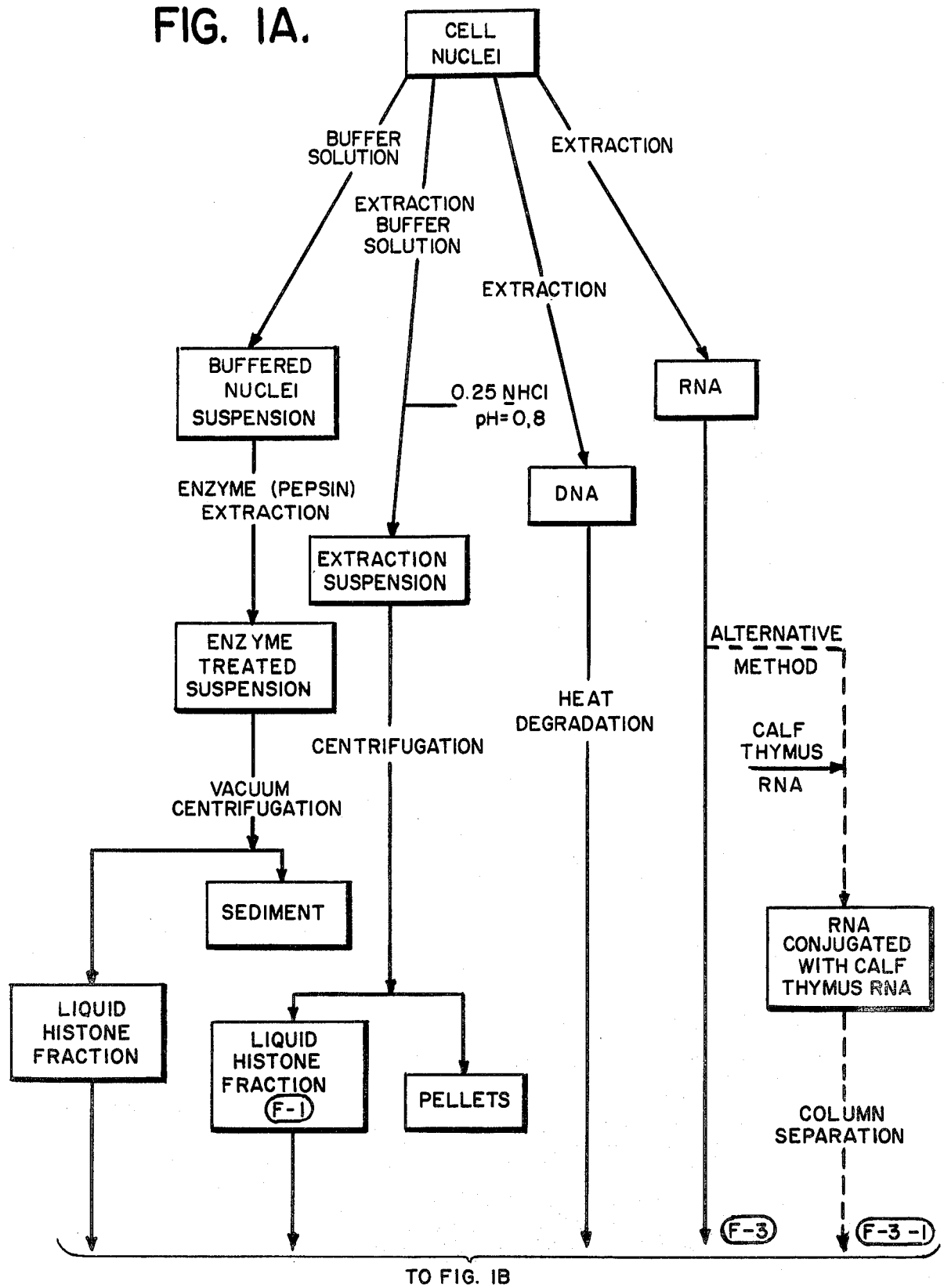
Figure 1B:
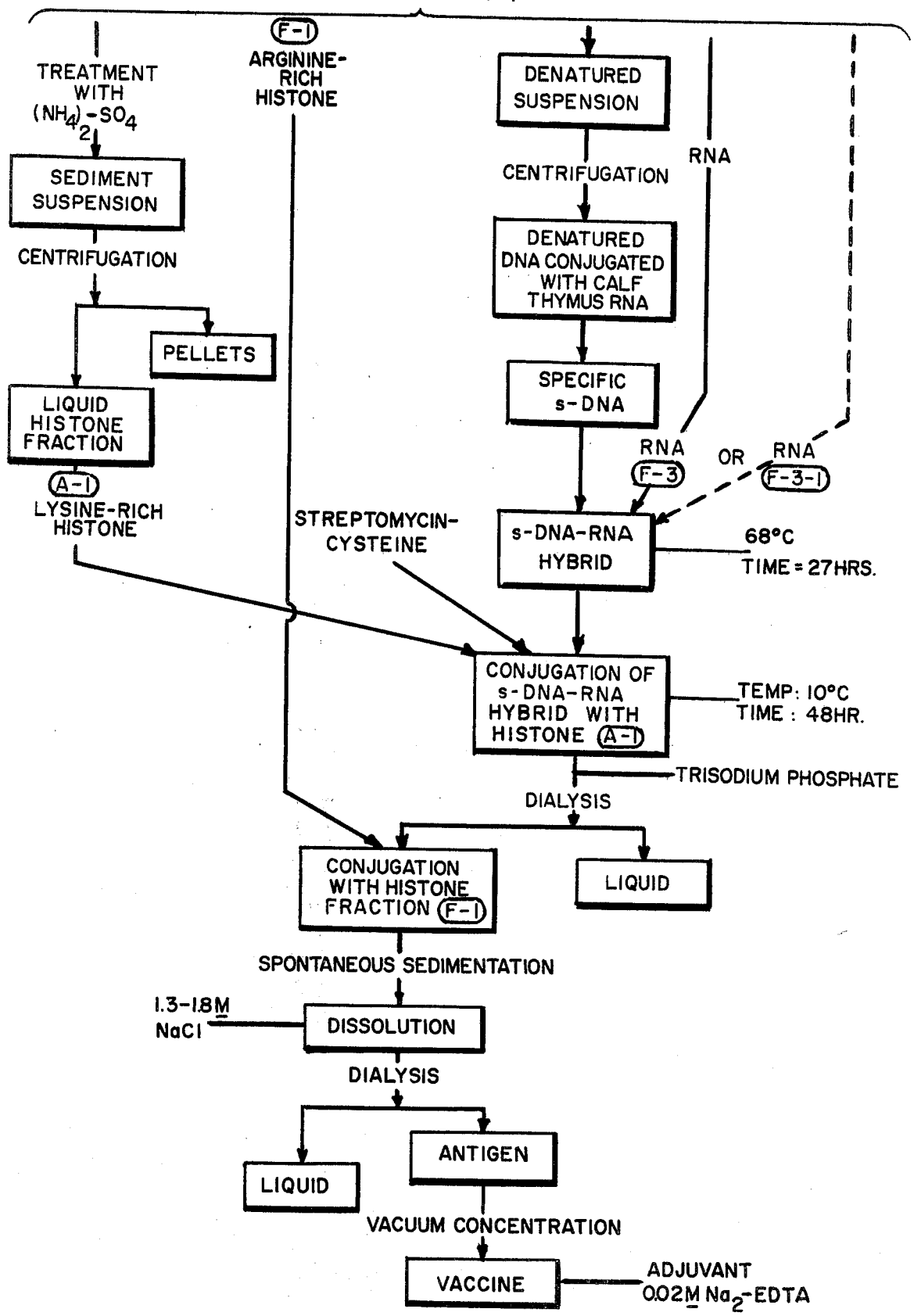

FIG. 1A and FIG. 1B illustrate a method of preparation which is especially suitable for preparing materials for the control of abnormal tissue growth in both animals and humans. In some instances, the parameters and data shown on the charts may differ in scope from the parameters and data set forth hereinbelow, and, to the extent of any such differences, the flow charts are intended to represent additional and further examples of the invention.

EXAMPLE 1

EXTRACTION(S) OF LYSINE RICH HISTONE FROM NUCLEI WITH ENZYME PEPSIN

A. Extraction with the Enzyme Pepsin

Pure nuclei from cancer cells are suspended and homogenized into the following buffer solution:
tri-sodium citrate: 19.62 g
concentrated HCl: 8.40 ml
thiodiglycol: 5.00 ml
distilled water: 1000 ml The experimental conditions are: temperature, 4° C.; buffer pH, 2.4; wt. ratio of buffer to cell nuclei, 4.1; homogenization, 5000 rpm; time, 30 seconds.

Pepsin, 0.8–1% by weight of the pure nuclei, is added to the homogenate. The mixture is stirred under vacuum or nitrogen for six hours at a temperature of 18°–24° C.; pH of 2.8–3.4.

The pepsin extracted product is centrifuged at 20,000 rpm at 2°–4° C. for 45 minutes. The sediment and supernatant liquid are analyzed for DNA, RNA and protein content by conventional methods. The sediments are saved for further processing as described in Step C below.

B. Recovery of Histone and Extracted Nuclei

The supernatant liquid from the extraction described above is precipitated with an equal volume of saturated ammonium sulfate solution at −10° C. for 12 hours. Ammonium sulfate having a ferrous ion content no higher than 0.001% is used.

The precipitate is separated by centrifugation at 15,000 rpm for 45 minutes at a temperature of −10° C. The supernatent liquid is discarded.

The sediment is dissolved in 0.1 M citrate-phosphate buffer solution having a pH of 3.6 and is subjected to dialysis against 0.001 M citrate-phosphate buffer solution having a pH of 3.6. The dialysis is continued for as long as ammonium sulfate is separated.

After the dialysis step above described, the solution is filtered through a "Millipore" filter, and the pH is adjusted to 5.6. The thus-obtained solution is identified as Histone Fraction A-1. The RNA, protein and amino-acid contents of the composition are determined. The histones of this Fraction A-1 are used for subsequent hybridization, as described below, with a s-DNA-RNA complex. Fraction A-1 contains histones which have a relatively high ratio of lysine to arginine.

c. Second Extraction with the Enzyme Pepsin

Steps A and B above are repeated using the sediments obtained from the pepsin extraction in Step A. The sediments from Step A of this second pepsin extraction are used as raw material in Example 2 below. The lysine rich histones in the supernatant liquid are recovered and purified as in Step B above to give Histone Fraction A-2.

EXAMPLE 2

EXTRACTION OF ARGININE RICH HISTONE

Pure cancer cell nuclei are homogenized in 4 parts of the following buffer solution:

0.14 M NaCl
0.02 M EDTA—sodium salt (di-sodium ethylenediaminetetraacetate)
0.02 M $Na_2HPO_4$ The homogenization is carried out at a temperature of 0°–6° C. for 10 seconds at 1,500 rpm; the pH of the homogenate is maintained at 6.4 to 6.8. Following the homogenization, the homogenate is stirred for 5 to 10 minutes. The cell nuclei are recovered by centrifugation (35,000 G) at a temperature of 0°–6° C. for 20 to 30 minutes.

An arginine-rich histone fraction is then recovered from the washed cell nuclei by extraction with the following solution:

0.14 M NaCl
0.02 M sodium citrate
0.25 M HCl (free from ferrous ions)

The nuclei and eight parts of the solution by weight are homogenized for 30 seconds at 0°–6° C. at a stirrer speed of 5,000–6,000 rpm. The homogenate is then slowly stirred at 0°–4° C. for a period of 12 hours.

The histone fraction is recovered from the above homogenate by centrifugation at 0°–6° C. for 45 minutes using a centrifugal force at 75,000 G. The supernatant liquid is removed by filtration. The pH of the filtered solution is adjusted to 3.2 with 2-mercaptoethanol. The product, identified as Fraction F-1, is analyzed for total protein and amino-acid content. It is stored at 1° 4° C. for future use.

EXAMPLE 3

ISOLATION OF CANCER-ACTIVE s-DNA BY HYBRIDIZATION OF CANCER CELL d-DNA WITH RNA FROM NORMAL THYMUS CELLS

A. Isolation of Cancer-cell s-DNA

Nuclear DNA is isolated by any of the methods cited above. The procedure used is not critical to the invention, and accepted literature procedures other than those cited may be used. It is essential, however, that the DNA used for subsequent denaturation contain no RNA and the amount of protein present be less than 0.5% that of the DNA.

The phenol extraction procedure of Kirby for isolation of DNA requires about 24 hours. With this procedure it is necessary that the isolation of DNA is completed without prolonged storage of the material at any of the stages. For example, storage for twelve hours leads to a dcrease in DNA yield of 30–38% and a decrease in activity of s-DNA derived therefrom of 50 to 80%. Before the first treatment of the material with phenol it is advantageous to treat it with sodium lauryl sulfate. It is strictly necessary for pharmacological purposes to remove all traces of phenol. This can be done by: (1) using Sephadex 25 absorption or (2) by flushing with nitrogen following the addition of 0.2 volumes of ether.

The final concentration of DNA obtained should not exceed 500 mg/ml in order to avoid agglomeration and deactivation. Lyophilization is not recommended, because the solubility is strongly decreased.

Denaturation of DNA by the method of Albertson cited above, may be used, as well as other well recognized procedures. The following procedure contains reaction and quality control parameters which will yield denatured DNA suitable for isolation of the cancer active single-stranded DNA: Extracted DNA is diluted with 0.02 molar phosphate buffer solution having a pH of 7.4 to give a DNA concentration of between 400 and 500 gamma/milliliter. The concentration of the DNA solution is determined by spectrophotometric measurement at 260 millimicrons. This solution is diluted with four parts water prior to denaturation to give a concentration of 100 to 125 gamma DNA per milligram in an aqueous solution containing the following materials and approximately the following concentrations:

0.005 M $NaH_2PO_4$
0.0025 M $Na_2HPO_4$
0.001 M EDTA
0.001 NaOH

The pH of the solution is 6.7 to 6.9. It is heated to the melting point of DNA at a rate to give a temperature rise of 3–4 centigrade degrees per minute, after which the temperature is held constant for 10–20 minutes. The solution is then cooled rapidly in about 2–10 minutes to a temperature of 0°–4° C. After cooling the solution, 0.002 volumes of 36–40% aqueous solution of formaldehyde is added.

The temperature for melting of DNA is different for the different tissues and organs from which it is isolated. For example, for DNA which is isolated from the cell nuclei of Sarcome Yoshida from rats, the melting temperature is 95° C.

B. Hybridization of $d-DNA_c$ with $RNA_n$

The RNA required for hybridization is obtained from calf thymus gland tissue; it is isolated in accord with standard procedures detailed and described by authors cited previously.

An equal-molar quantity of RNA isolated from calf thymus gland tissue is added to the solution of denaturized DNA from Step A above. The mixture in 0.25 M NaCl is stirred slowly from about 56° to 68° C. for a period of 16 to 24 hours.

C. Isolation of Cancer-Active s-DNA from the Hybridization Reaction Mixture

A chromatographic column filled with high purity hydroxyapatite is washed with two volumes of a 0.005 M phosphate buffer having a pH of 7.0. The solution from Step B is then passed through the column. The non-bonded RNA, the non-specific DNA genome which is now hybridized with RNA, and the non-hybridized DNA (cancer-specific genome) are retained on the column.

The RNA and the DNA-RNA hybrid are first eluted by washing the column with two volumes of the 0.005 M phosphate buffer used to balance the column.

The active, single-stranded DNA is then recovered by eluting the column with a 0.1 to 0.2 M sodium phosphate buffer having a pH of 7.2. The eluted product is identified as Fraction F-2.

The entire chromatoraphic separation is carried out at 2° to 6° C. under sterile conditions.

The cancer active s-DNA is recovered in a yield of 75–80%. The DNA content, the total protein content and the molecular weight of the DNA are determined. If the protein content is more than 0.8% than of DNA, the DNA solution must be treated with proteinase followed by deproteinization by passage through a column packed with Sephadex G-50.

Ultra-violet absorption curves give extinction peaks with the following ratios: $E_{260}/E_{230} \geq 3.0$, and $E_{260}/E_{280} \geq 1.9$.

EXAMPLE 4

ISOLATION OF CANCER ACTIVE RNA

Methods of isolating nuclear RNA from cell nuclei from normal or cancer tissues are well known. Examples of such methods in the literature are those of Kimura, Georgiev or Kirby as cited previously.

RNA obtained from cancer cell nuclei is dissolved in a 0.15 M sodium chloride solution containing 0.5 mg of polyvinyl sulfate per ml of salt solution. The solution is identified as Fraction F-3.

The concentration of the RNA should be 100-150 gamma per ml of solution. Ultra-violet absorption measurements give extinction peaks with the following ratios: $E_{260}/E_{230} \geq 2.3$ and $E_{260}/E_{280} \geq 2.0$. The sedimentation constant, $S_{20}$ (Svedberg number), varies between about 4 and 8, depending on the source of starting material and tumor type.

When the percentage of the non-cancer type RNA in the RNA which is isolated from cancer cell nuclei is above about 15%, it is preferred to concentrate the cancer-active RNA by hybridization with d-DNA isolated from calf thymus gland tissue. The procedure generally follows that used in isolating the single-stranded active DNA genome as described in Step B above. Differences from the procedures cited in these steps are as follows:

Hybridization time is 18 to 24 hours. The pH of the hybridization mixture is 6.2 to 6.8.

The first elution with 0.005 M phosphate buffer contains the cancer-specific RNA. The RNA is recovered in a yield of about 80% of the active material present in the total RNA obtained. The concentration of the eluted product is adjusted to 100-150 gamma per ml of solution. The RNA solution is identified as Fraction F-3.

EXAMPLE 5

PREPARATION OF THERAPEUTIC NUCLEOPROTEIDE COMPLEX BY RECOMBINATION OF CANCER-ACTIVE s-DNA$_c$ WITH CANCER-ACTIVE RNA, LYSINE-RICH HISTONES AND ARGININE-RICH HISTONES

The reactant ratios of the four fractions (A-1, F-1, F-2 and F-3) used for recombination are determined by the relative amounts of cancer-active DNA and cancer-RNA of the animal tumor (used for vaccine) which react with DNA and RNA of the human tumor being treated. The reactant ratios used in the following hybridization procedures are selected in accord with principles set forth heretofore.

A. Hybridization of s-DNA$_c$ with RNA$_c$

Fraction F-2 from Step B of Example 3 and Fraction F-3 from Example 4 are combined and the mixture is heated to 58°-62° C. It is held at this temperature for 18-24 hours to assure complete formation of the s-DNA$_c$-RNA$_c$ complex.

B. Hybridization of s-DNA$_c$-RNA$_c$ Complex with Lysine-rich Histones

The complexed s-DNA-RNA from Step A above is cooled to 0°-6° C. With continuous stirring, the lysine-rich histone (A-1) dissolved in a 0.005 M solution of streptomycin-cysteine is slowly added to the cold DNA-RNA complex solution over a period of 6-12 hours. One mg of streptomycin-cysteine is used per mg RNA. The pH of the resulting solution is corrected to 4.0-4.2 with 1 M sodium acetate, and 5 ml of thiodiglycol is added per 1,000 ml material. The temperature is increased to 8°-12° C., and an alcoholic solution of periodic acid, (2.4 gm of periodic acid per 1000 gamma of nucleic acids) is added, and the mixture is incubated with continuous stirring for 6-12 hours at 2°-4° C.

The pH of the incubated mixture is adjusted to 7.6 with a 1 M solution of tri-sodium phosphate. It is dialyzed against deionized water until complete removal of iodine is obtained. A 0.1 volume of 20% aqueous potassium citrate solution is then added.

The resulting nucleohistone complex (histone/s-DNA/RNA) is precipitated with 2.5 volumes of absolute ethanol at $-8$ to $-12°$ C. over a period of 6-12 hours. The precipitated complex is separated by centrifugation at 10,000 g, 10,000 rpm, for 40 minutes at 0°-6° C. The recovered sediment is dissolved in 3 parts of a 0.1 M citrate-phosphate buffer of pH 3.8 containing 0.1 mole of sodium chloride.

C. Hybridization of Histone-(s-DNA$_c$)-RNA$_c$ Complex with Arginine-Rich Histones The complex from Step B above is stirred at 8°-12° C. while arginine-rich protein Fraction F-1 is added to it slowly over a period of 6-10 hours. If the pH of the solution is below 3.3, the solution is adjusted to 3.3 to 3.5 with a 0.25 M tri-sodium phosphate solution. The solution is then cooled to 0°-6° C. and held at this temperature for 12-24 hours with continuous stirring to precipitate the recombined nucleoproteide. When preparing anticancer vaccine against malignant melanoma, the incubation time is increased to 48 hours.

To achieve a complete combining of the nucleic acids with the protein, the latter must exceed by about 5-8% the quantity necessary for the complete saturation (conjugation) of the nucleic acid complex.

The reconstituted nucleoproteide complex is separated by centrifugation at 14,000 g, 12,000 rpm for 60 minutes at 0°-6° C. The sediment is placed into 1 M solution of NaCl, containing 3-mercaptoethanol (5%). Ratio of sediment to solvent (wt/wt) is 1:6.

The DNA, RNA and protein content of the new complex is determined. This initial analysis is especially important to establish the composition of each type of anticancer vaccine and to assure that the optimum ratio of combining nucleic acids and Fraction F-1 is used in the hybridization.

EXAMPLE 6

PREPARATION OF VACCINE CONTAINING RECONSTITUTED NUCLEOPROTEIDE COMPLEX

The nucleoproteide complex from Example 5 is mixed with 6 parts of a 1 M sodium chloride solution containing 5 wt. % of 2-mercaptoethanol. The mixture is stirred slowly under an inert nitrogen atmosphere at 0°-4° C. for 12 hours. If the complex is not completely dissolved at the end of this time, the NaCl content is increased to a final concentration 1.3-1.8 M. The total time for dissolving the nucleoproteide must not exceed 24-30 hours.

The solution from above is filtered through a "Millipore" filter suitable for high molecular weight compounds. The disodium salt of EDTA is then added to give 0.1 molar concentration. The resulting solution is dialyzed against deionized water containing 0.02 M EDTA which is changed every two hours. The dialysis is carried out at temperature of 2°-6° C. until the concentration of sodium chloride is reduced to 0.1 molar.

The DNA, RNA and total protein content of the dialyzed solution is determined. The total quantity of nucleic acid included in the final therapeutic product varies between about 700 and 1400 gamma per ml of product. If it is necessary to concentrate the dialyzed solution, it can be done by low-temperature vacuum distillation, by dialysis, or by filtration.

Concentration of the product by dialysis is carried out at 0° to 4° C. against a 30% solution of polyvinylpyrrolidone having a molecular weight of 25,000.

The dialyzed product is tested for sterility and pyrogenic properties. The concentrations of nucleic acids, proteins and Na and Cl ions are determined.

The content of Na ions in the dialyzed product is adjusted to a concentration equivalent to 0.2 M NaCl. The pH is adjusted to 4.8 with a 0.2 N HCl solution before adding 2-mercaptoethanol, 38-40% aqueous solution of formaldehyde, K-citrate, polyvinylpyrrolidone and merthiolate in quantities sufficient to give the following final concentrations:

2-mercaptoethanol; 0.5%
formalehyde: 0.4%
K-citrate: 0.02 M
polyvinylpyrrolidone: (mol. wt. 48,000—4%)
merthiolate: 1:10,000–1:15,000
glycerol: 0.3–0.8%

The product is passed through a filter suitable for solutions of high molecular weight materials.

An approved U.S. Pharmacopoeian adjuvant is added to the filtrate. A preferred adjuvant is aluminum hydroxide added in the amount of 25 mg/ml of solution.

Storage of final therapeutic product for an extended period of below 0° C. down to −25° C. can be accomplished by the addition of less than 1% glycerol.

For vaccines which are used for treatment of animals, Freund's adjuvant is a preferred adjuvant.

The products of the invention may be formulated for clinical use in a number of ways which are not intended to limit the scope of the invention. Other inactive components may also be added to the active constituents to give the vaccine, as follows:
0.14 molar sodium chloride, plus
1 percent polyvinylpyrrolidone or
1.5 molar sodium chloride, plus
0.15 potassium citrate.

In addition to the above, each milliliter of vaccine contains 25 milligrams of adjuvant.

EXAMPLE 7
PROCESS VARIATIONS

As in normal chemical processes, the reactant ratios and process steps may be varied to produce a given specific product or composition. This possibility also exists for the preparation of the compositions of the invention. The following process variations of hybridization are typical examples of methods which have been used to prepare effective vaccines:

I. RNA and s-DNA are first hybridized, and this step is followed, first by addition of the lysine-rich histone fraction (LRF) and then by addition of the arginine-rich histone fractions (ARF). (Procedure of Examples 1–6 above as reference.)

II. RNA and LRF are bonded together into a weak complex in the presence of streptomycin-cysteine, s-DNA is then added; and this step is followed by the addition of ARF.

III. RNA, LRF and ARF are brought together in a competitive reaction in the presence of streptomycin-cysteine, and this procedure is followed by the addition of s-DNA.

IV. ARF and streptomycin-cysteine are heated together prior to the addition of RNA and LRF. After incubation, the LRF-RNA-ARF-streptomycin-cysteine complex is precipitated with trichloroacetic acid to a final trichloroacetic acid concentration of 5%. The resulting precipitate is dissolved and then hybridized with s-DNA.

A further variation is required for preparing vaccines for the treatment of RNA-virus induced cancers in which the amount of the cancer-active DNA genome is small. An example of this is the vaccine for liver cancer, Preparation 7, Table 1, hereinbefore referred to, in which the amount of cancer-active DNA in the liver cancer is only 0–3% of the total DNA. To prepare a stable, effective vaccine, s-DNA from normal calf thymus is caused to replace the active s-DNA that would have been used for hybridization with RNA had it been present in the preferred transplantable animal tumor.

Suitable procedures for the above process variations citing the principal reaction conditions are illustrated below; the reference Roman numerals (I, II, etc.) identify the product from the given process step, which product is used in subsequent steps.

PROCEDURE 7A
DNA Virus Cancers
Starting Materials

1. Equal quantities of s-DNA, RNA, LRF and ARF at concentration of 600 gamma/ml.; 150 ml. each
2. Streptomycin-cysteine (S/C) 5,000 gamma/ml; 30 ml

Process Steps

3. S/C added to RNA t 37°; pH 8.2 (I)
4. LRF added to (I) at 20°; cooled to 4°; 1 hr. (II)
5. DNA added to II at 4°; pH 5.6; 4 hrs. (III)
6. (III) heated to 56°; pH 5.6; 24 hours; cooled to 4° (IV)
7. (IV) solubilized in 2 M NaCl; dialized against dist. water, 24 hr. (V)
8. LRF.DNA.RNA pptd. at −10° with 2.5 vol. ethanol per vol. (V), 12 hr.; centrifuged, 40,000 G (VI)
9. (VI) dissolved in buffer, pH 5.6 and ARF fraction is added; ppt. centrifuged at 12,000 G (VII)
10. VII dissolved in 2 M NaCl (1:5 ratio); dialyzed against dist. water, 24 hr.; and pH adjusted to 6.2 with thiodiglycol (to 0.42 M) and sodium citrate (to 0.015 M) (VIII)

Composition of (VIII), gamma/ml.

DNA, 444; RNA, 173; total protein, 1.678.
Wt. ratio DNA/RNA, 2.57.
Wt. ratio protein/nucleic acids, 2.72.

PROCEDURE 7B

A variation of the above procedure is useful for preparing vaccines against RNA-virus induced cancers. Changes in the reactant quantities and Steps 3–10 of Procedure 7A above follow:

Starting Materials (150 ml of each reactant; concn. in gamma/ml)

1. s-DNA, 180; RNA, 1000; LRF, 410; and ARF, 380/

Process Changes

7. Dialysis against water is omitted (V)
8. ARF is added to (V) followed by dialysis against dist. water, 24 hr. (VI)
9. (VI) is pptd. with ethanol as in Step 8 above, followed by centrifugation, solubilization in 0.14 M NaCl and adjustment of pH to 6.8 (VII)

Composition of (VII), gamma/ml.

DNA, 83; RNA, 696; total protein, 925
Wt. ratio DNA/RNA, 0.12
Wt. ratio protein/nucleic acids, 1.19

PROCEDURE 7C

Cancer-Active RNA Cancers

Starting Materials

1. Equal volumes of following reactants (concentrations in gamma/ml): s-DNA, 180; RNA, 1,000; LRF, 800; ARF, 800. (150 ml. each).
2. Streptomycin-cysteine, 5,000 gamma/ml., 30 ml Process Steps 1. S/C added to RNA at 37°; pH 8.2; 10 min. (I)
2. LRF added to (I) at 20°; cooled to 4°; 1 hr. (II)
3. ARF added to (II) at pH 5.6, 37°; 4 hr. (III)
4. III at pH 2.4 (formic acid held at 4°, 12 hr) (IV)
5. s-DNA is added to (IV), 4 hr.; temp. increased to 56°; 24 hrs.; pH 3.8 (V)
6. (V) is pptd. with 2.5 vol. ethanol at $-10°$ (VI)
7. (VI) is recovered by centrifugation, 40,000 G, and dissolved in NaCl (to 0.14 M) and pH adjusted to 6.2 with thiodiglycol (to 0.42 M) and sodium citrate (to 0.015 M). (VII)

Composition of (VII), gamma/ml

DNA, 76; RNA, 456; total protein, 725
Wt. ratio DNA/RNA, 0.17
Wt. ratio protein/nucleic acids 1.37

PROCEDURE 7D

The detailed process procedures given in Examples 1-6 hereinabove may also be used to prepare active vaccines using calf-thymus s-DNA for treatment of RNA-VIRUS cancers containing little or no cancer-active DNA genome. It has been found essential to use the normal, calf-thymus DNA to obtain a stable complex containing LRF and ARF.

A typical example is the preparation of a vaccine for cancer of the liver containing less than 3% active DNA. The reactant ratios are changed to the following:

Calf-thymus s-DNA: 180 gamma/ml
Yosida RNA, 4.8S: 1000 gamma/ml
LRF: 400 gamma/ml
ARF: 1,500 gamma/ml The reaction conditions and procedure described in Examples 1 through 5 herein above are used.

The vaccine had the following composition, in gamma/ml.

DNA, 180; RNA, 950; LRF, 400; ARF, 1493
Wt. ratio DNA/RNA, 0.19
Wt. ratio protein to nucleic acids: 1.67

TREATMENT OF CANCER

TESTING AND USE OF THE COMPOSITIONS

Data set forth below in Tables 12, 13, 14, 15, 16 and 17 show the utility of the invention as applied to the treatment of both animals and humans.

EXAMPLE 8

ANIMAL TESTS

The results of testing the therapeutic products with 2,150 mice, rats and hamsters are summarized in Tables 13 and 14 hereinbelow.

Abbreviations used in the Tables define the type of cancer, the animal used, the dose regime in treating the animal, the route of administering the vaccine, and the internationally accepted method used in calculating the effectivity of the vaccine. The abbreviations so used are defined and fully identified in Table 12.

Effectiveness of the vaccine was evaluated using the accepted International method of comparing the mean weight of the tumors from the treated animals with the tumors from the untreated controls. All animals were sacrificed at the time of death of the last animal in the control group. The tumors were excised, debrised, weighed and averaged. The percent effectivity of the treatments is expressed as $100-100 (T/C)$, in which T = The mean tumor weight of the test animals
C = The mean tumor weight of the control animals Effectivity results of 70% or higher demonstrate high activity in the material being tested. Effectivities of 80% or higher are considered sufficient evidence of activity to warrant clinical trials with the therapeutic material exhibiting such results.

Most immunopharmacological agents exert quite diverse effects on immune reactions, depending on dosage, time and route of administration. Consequently the tests summarized in Table 13 were programmed using combinations of three different routes of administration with three different dosage regimes. As expected, differing degrees of effectiveness resulted; however, all treatment combinations gave tumor regression. Certain treatment combinations gave significantly high percentages of tumor regression for each of the ten different types of tumors used for testing. Effectivity results were between 71 and 97% for the ten tumors tested.

The most effective method of administration was intramuscular injections using the programmed regime (3) of Table 12. Intraperitoneal injections of the vaccine also resulted in high rates of tumor regression. This is shown in Table 14 which summarizes the two most effective treatment combinations for each tumor.

TABLE 12

| ANIMAL TESTS |
|---|
| Explanation of Abbreviations |
| (All animals sacrificed at death of last control animal in group) |

| Host Animals (H) | |
|---|---|
| 1—DBA | 12—Fischer/344 |
| 2—C3H | 15—Wister |
| 3—C57G | 21—Syrian Hamster |
| 4—Swiss | |
| Number of Animals in Group | |
| NC—Control | NT—Test |
| Tumor Test System (TS) | Animal Lines: |
| MSV—Moloney Sarcoma Virus | Mice: DBA, C3H, C57B |
| FVL—Friend Virus Leucemia | Rats: Fischer/344, |
| LE—Lymphoid Leukemia 1210 | Wister |
| SA—Sarcoma 180 | Hamsters: Random bred |
| HP1—Hepatoma | |

TABLE 12-continued
ANIMAL TESTS

A/1—Sarcoma Yoshida
H/1—Rhabdomyosarcoma
H/2—Melanotic Melanoma
H2A—Amelanotic Melanoma
H/4—Adenocarcinoma Dose Regime (DR)
1—Every day   2—Every other day
3—Basic scheme: 101000100000110000001110000001110000001110000001110000000000111

Route of Administration (RA)
1—Intramuscular (i.m.)
2—Intraperitoneal (i.p.)
3—Intravenous (i.v.)

Average Dosages of Vaccines (from 4 mice; from 2 rats; 4 hamsters)

Mice: 100 Gamma DNA, 70 Gamma RNA, 80 Gamma Protein
Rats: 200 Gamma DNA, 120 Gamma RNA, 160 Gamma Protein
Hamsters: 180 Gamma DNA, 110 Gamma RNA, 110 Gamma Protein

TABLE 13
ACTIVITY OF VACCINE IN ANIMAL TESTS - EFFECT OF TREATMENT COMBINATIONS ON % EFF.

| H | TS | NT | NC | DR | RA | T/C. 100 | % EFF. |
|---|-----|----|----|----|------|----|----|
| 1 | FVL | 25 | 25 | 1 | i.m. | 83 | 17 |
| 1 | FVL | 25 | 25 | 1 | i.v. | 88 | 12 |
| 1 | FVL | 25 | 25 | 3 | i.m. | 11 | 89 |
| 1 | FVL | 25 | 25 | 3 | i.v. | 41 | 59 |
| 2 | MSV | 25 | 25 | 1 | i.m. | 73 | 27 |
| 2 | MSV | 25 | 25 | 3 | i.m. | 21 | 79 |
| 2 | MSV | 25 | 25 | 3 | i.v. | 39 | 61 |
| 2 | LE | 25 | 25 | 1 | i.m. | 76 | 24 |
| 2 | LE | 25 | 25 | 1 | i.m. | 85 | 15 |
| 2 | LE | 25 | 25 | 3 | i.m. | 22 | 78 |
| 2 | LE | 25 | 25 | 3 | i.p. | 33 | 67 |
| 2 | LE | 25 | 25 | 3 | i.v. | 37 | 63 |
| 4 | SA | 25 | 25 | 1 | i.m. | 24 | 76 |
| 4 | SA | 25 | 25 | 1 | i.p. | 58 | 42 |
| 4 | SA | 25 | 25 | 2 | i.m. | 19 | 81 |
| 4 | SA | 25 | 25 | 3 | i.m. | 57 | 43 |
| 4 | SA | 25 | 25 | 3 | i.p. | 23 | 77 |
| 12 | HP1 | 25 | 25 | 1 | i.m. | 47 | 53 |
| 12 | HP1 | 25 | 25 | 2 | i.m. | 52 | 48 |
| 12 | HP1 | 25 | 25 | 3 | i.m. | 21 | 79 |
| 12 | HP1 | 25 | 25 | 3 | i.p. | 24 | 76 |
| 15 | A/1 | 25 | 25 | 1 | i.m. | 14 | 86 |
| 15 | A/1 | 25 | 25 | 1 | i.p. | 22 | 78 |
| 15 | A/1 | 25 | 25 | 2 | i.m. | 17 | 83 |
| 15 | A/1 | 25 | 25 | 3 | i.m. | 39 | 61 |
| 15 | A/1 | 25 | 25 | 3 | i.p. | 69 | 31 |
| 21 | H/1 | 25 | 25 | 2 | i.m. | 30 | 70 |
| 21 | H/1 | 25 | 25 | 2 | i.p. | 19 | 81 |
| 21 | H/1 | 25 | 25 | 3 | i.m. | 47 | 53 |
| 21 | H/1 | 25 | 25 | 3 | i.p. | 20 | 80 |
| 21 | H/2 | 25 | 25 | 1 | i.m. | 54 | 46 |
| 21 | H/2 | 25 | 25 | 1 | i.p. | 19 | 81 |
| 21 | H/2 | 25 | 25 | 3 | i.m. | 3 | 97 |
| 21 | H/2 | 25 | 25 | 3 | i.p. | 25 | 75 |
| 21 | H2A | 25 | 25 | 1 | i.m. | 87 | 13 |
| 21 | H2A | 25 | 25 | 1 | i.p. | 62 | 38 |
| 21 | H2A | 25 | 25 | 3 | i.m. | 29 | 71 |
| 21 | H2A | 25 | 25 | 3 | i.p. | 29 | 71 |
| 21 | H/4 | 25 | 25 | 1 | i.p. | 69 | 31 |
| 21 | H/4 | 25 | 25 | 2 | i.m. | 80 | 20 |
| 21 | H/4 | 25 | 25 | 2 | i.p. | 91 | 9 |
| 21 | H/4 | 25 | 25 | 3 | i.m. | 41 | 59 |
| 21 | H/4 | 25 | 25 | 3 | i.p. | 28 | 72 |

TABLE 14
EFFECTIVE TREATMENT REGIMES

| Tumor | 1st % Eff. (Regime) | 2nd % Eff. (Regime) |
|---|---|---|
| 1. Friend Virus Leucemia | 89 (3-i.m.) | 59 (3-i.v.) |
| 2. Moloney Virus Sarcoma | 79 (3-i.m.) | 61 (3-i.v.) |
| 3. Lymphoid Leucemia 1210 | 78 (3-i.m.) | 67 (3-i.p.) |
| 4. Sarcoma 180 | 81 (2-i.m.) | 77 (3-i.p.) |
| 5. Hepatoma | 79 (3-i.m.) | 76 (3-i.p.) |
| 6. Sarcoma Yoshida | 86 (1-i.m.) | 63 (2-i.m.) |
| 7. Rhabdomyosarcoma | 81 (2-i.p.) | 80 (3-i.p.) |
| 8. Melonotic Melanoma | 97 (3-i.p.) | 81 (1-i.p.) |
| 9. Amelonotic Melanoma | 71 (3-i.m.) | 71 (3-i.p.) |
| 10. Adenocarcinoma | 72 (3-i.p.) | 59 (3-i.m.) |

EXAMPLE 9
CLINICAL STUDIES

Clinical Tests—Method of Treatment

The immunotherapy compositions of the invention may be administered by intravenous, intraperitoneal or intramuscular injection. The preferred method is by intramuscular injection.

The basic course of initial treatment is preferably administered according to the following scheme:

100100001000000110000011100000011100000011100-000011100000011100000011100000111, in which "1" stands for the days of application of the vaccine and "0" for the days of non-application of the vaccine.

It is usually possible to discharge the patient from the hospital during the third to sixth week of treatment and thereafter continue the treatment on an out-patient basis.

Following the initial treatment, three reimmunizations are given as follows:

First-Reimmunization—three months after the end of the initial basic course of treatment Second-Reimmunization—six months after the end of the first-reimmunization Third-Reimmunization—nine months after the end of the second-reimmunization All reimmunizations are given according to the following scheme:

10110001110000001110000001110000001110000000-00011

The dosage of each application of the vaccine varies with the different vaccines used to treat the different kinds of cancer disseminations, with the majority of the vaccines falling within the ranges:

From 400 to 800 Gamma DNA
From 200 to 700 Gamma RNA
From 800 to 2,000 Gamma Protein.

The concentrations of the active ingredients are routinely adjusted to give the required dosage in the one milliliter of the vaccine used in each application.

Clinical Treatments—Results

Clinical survival data of vaccine treated patients are set forth in Tables 15, 16, and 17. Only patients in Stage III or IV of cancer development have been treated with the vaccine. Group III patients are those patients treated by surgery alone, or in combination with radiation and/or chemotherapy, who developed distant cancers in other body tissues within 1-3 years after the initial treatment. Group IV patients are those patients with metastatic cancers too far advanced when diagnosed for treatment with known methods.

The Case Histories—Summaries of clinical data which were included in Table 16 and which comprised originally numbered pages from 66 to 78 (renumbered by amendment as pages 73 to 85) of parent copending application Ser. No. 861,072 of which this application is a continuation-in-part are totally incorporated hereby by reference.

TABLE 15

SUMMARY OF CLINICAL STUDIES WITH COMPOSITIONS OBTAINED FROM ANIMAL TUMORS (1970-1973)

Metastasis confirmed in all patients by microscopic examination of cell tissues.

TREATMENT AND REIMMUNIZATION ONLY WITH VACCINES FROM ANIMAL TUMORS USING FOLLOWING VACCINES

| Name | Group | Treatment Started | 1975 | 1978 | Sv. T. Yrs. |
|---|---|---|---|---|---|
| Breast Cancer | | | | | |
| E.M. | III | IV, 1971 | Livg | Livg | 7 |
| I.C. | III | IX, 1971 | Livg | Livg | 6 |
| D.S. | IV | I, 1972 | Livg | Livg | 6 |
| A.C. | III | VIII, 1973 | Livg | Livg | 5 |
| Lymphogranulomatosis - Hodgkin's Disease | | | | | |
| D.P. | III | VIII, 1972 | Livg | Livg | 6 |
| Lymphosarcoma - Children's Hospital, Moscow | | | | | |
| S.B. | IV | XII, 1972 | Livg | Livg | 6 |
| Stomach Adenocarcinoma - Dist. Hosp., Patch, Hungary | | | | | |
| I.K. | III | XI, 1972 | Livg | Livg | 6 |
| Lg. Intestine - Adenocarcinoma | | | | | |
| MM. | IV | I, 1973 | Livg | Livg | 5 |
| Lung | | | | | |

TABLE 15-continued

SUMMARY OF CLINICAL STUDIES WITH COMPOSITIONS OBTAINED FROM ANIMAL TUMORS (1970-1973)

Metastasis confirmed in all patients by microscopic examination of cell tissues.

TREATMENT AND REIMMUNIZATION ONLY WITH VACCINES FROM ANIMAL TUMORS USING FOLLOWING VACCINES

| Name | Group | Treatment Started | 1975 | 1978 | Sv. T. Yrs. |
|---|---|---|---|---|---|
| J.B. | IV | I, 1970 | Killed in auto accident, Sept., 1971 | | 1 |
| Glioma Multiformae (1) | | | | | |
| D.P. | IV | 1966 | Livg in 1974 (last medical check) | | 7 |

(1) Initial 1966 treatment with vaccine prepared from human cancer tissue of process in co-pending application Ser. No. 946,010 Process 1, page 23 hereof. 1967 Reimmunization with vaccine prepared from animal cancer tissue of Process 2, page 23 hereof. 1968, 1969 and 1970 reimmunizations with vaccines prepared by the process described herein.

Examples of animal tumors used to prepared the vaccines for treatment of patients in Table 15 are:

Breast Cancer: Vaccine from Yoshida sarcoma in white rats.

Hodgkins's disease: Vaccine from NKL in white mice.

Lymphosarcoma: Vaccine from lymphosarcoma in white rats.

Stomach cancer: Adenocarcinoma in Syrian hamsters.

TABLE 16

VACCINE TREATMENT OF PATIENTS WITH METASTATIC OR INOPERABLE CANCERS (1974-1979)

| PATIENT | CANCERS IDENTIFIED AT TIME OF INITIAL TREATMENT | INITIAL VACCINATION | STATUS 1979 |
|---|---|---|---|
| 1. | Stomach, lymph nodes and liver | 1974 | Alive |
| 2. | Testicle, prostate, lung | 1974 | Alive |
| 3. | Stomach, peritoneum | 1975 | Alive |
| 4. | Stomach, peritoneum | 1975 | Alive |
| 5. | Pancreas, liver | 1975 | Alive |
| 6. | Breast, lung, bone | 1976 | Alive |
| 7. | Gall bladder, liver | 1976 | Alive |
| 8. | Stomach, lymph nodes and liver | 1977 | Died 7th day |
| 9. | Stomach (81 yr. old; judged to old for operation) | Jan., '77 | Alive |
| 10. | Leukemia (5 yr. old), spleen and lymph nodes | Apr., '77 | Alive |
| 11. | Breast, lymph nodes | Jan., '78 | Alive |
| 12. | Melanoma pigmentosis of leg | Mar., '78[1] | Died, 15th day |
| 13. | Astrocytoma (brain) | Mar., '78 | Died, 34th day |
| 14. | Prostate, bone, lung | Aug., '78[2] | Died 30 days |
| 15. | Breast, bone (leg, arm) | Apr., '79 | Died, Dec., of pneumonia |
| 16. | Breast, skin | 1979 | Alive |
| 17. | Bladder, lymph nodes | 1979 | Alive |
| 18. | Large intestine, colon, abdomen and liver | 1979 | Alive |
| 19. | Lymphocytic leukemia, lymph nodes, spleen | Jun., '79 | Died, 11th day (3 yr. old) |

[1] Patient No. 12: Developed liver cancer 3-months after amputation of leg.
[2] Patient No. 14: 78 yrs. old; died 30-days after re-immunization.

In addition to the deaths occurring during the induction period following the start of the vaccination regime (7-21 days) which are set forth in Table 16 above, five patients treated during the 1972-1976 period died during the induction period. Including these five patients with those set forth in Tables 15, 16 and 17, a total of 46 patients were treated with the vaccine through Oct., 1979. Of these 46 patients, 30 are still living, 8 died during the induction period following start of vaccination, two died from other causes, and 6 died during first two years following start of treatment.

To assure the same survival times of 30 U.S. patients having the same cancers and metastatic stage of development as were present in the surviving Bulgarian patients, the treatment of over 600 U.S. patients would be required using the best available methods of treatment (Survival statistics from HEW Report cited previously).

TABLE 17

VACCINE TREATMENT OF LUNG CANCER PATIENTS
1970–1979

| PATIENT | INITIAL VACCINATION DATE | STATUS | MINIMUM SURVIVAL TIME |
|---|---|---|---|
| Lung 1 | Jan., 1970 | Died, Sept., '71 | —[1] |
| Lung 2 | Apr., 1972 | Died Jan., '77 | >4 yrs. |
| Lung 3 | Apr., 1972 | Died Sept., '75 | 3 yrs. |
| Lung 4 | Dec., 1973 | Alive Oct., '77 | >3 yrs. |
| Lung 5 | Dec., 1973 | Alive Oct., '77 | >3 yrs. |
| Lung 6 | Aug., 1974 | Alive Jan., '78 | >3 yrs. |
| Lung 7 | Mar., 1975 | Alive Sept., '78 | >3 yrs. |
| Lung 8 | Mar., 1975 | Died Oct., '77 | 2 yrs. |
| Lung 9 | Sept., 1976 | Alive Oct., '79 | >2 yrs. |
| Lung 10 | Nov., 1976 | Alive Oct., '79 | >2 yrs. |
| Lung 11 | Oct., 1979 | Alive Jan., '80 | — |

[1]Died in auto accident, Sept., 1971 (Included from Table 15)

In all of the cancer patients of Table 17 above, the initial lung cancer had spread to encompass both lungs or distant tissues before the time of the initial vaccination. The average survival time of patients 1–10 above is over 37.5 months. This is a significant increase in survival time over the average survival time of 9 months for all lung cancer patients in Bulgaria. It is more than twice the average survival time of 16 months for Bulgarian patients whose diagnoses in the early localized stages of the cancer development were followed by treatment with surgery, radiation, chemotherapy or hormones, or combinations thereof.

Comparison of the survival times of the patients treated with the vaccines of the invention with survival times obtained in the United States (Cancer Patient Survival, Report No. 5, 1976, HEW) also substantiates the remarkable effectiveness of the vaccines.

1. The median survival time for all lung cancer patients in the U.S. (1960–73) is less than 5.4 months. The median survival time of 39 months for the eleven patients of Table 16 is a significant result.
2. The survival of six of the eleven patients for over 3 years (with two still living two years after initial vaccination) is statistically significant in comparison with 3-yr. survivals of less than 2% for all U.S. patients, including those patients diagnosed in the localized stage.

The Bulgarian average survival time of 9 months (after initial diagnosis) for all lung cancer patients is less favorable than the 1960–73 U.S. experience of 11–14 months (HEW Cancer Patient Survival, Rpt. No. 5, 1976). The lower survival time of 9 months reflects a lower rate of initial cancer detection. This lack of early detection effect on the life expectancy has been documented in the HEW Report as contributing to the observed differences in the U.S. between the white (14 months) and black (11 months) populations. The results can be seen in 1, 3 and 5-year survival rates of all stages for both populations.

TABLE 18

COMPARATIVE SURVIVAL RATES
FOR ALL LUNG CANCER STAGES
1965—1965

| Survival Time | % Survival Rates | |
|---|---|---|
| | White | Black |
| 1-year | 27 | 23 |
| 3-year | 12 | 9 |
| 5-year | 9 | 6 |

Considering the lower probability of Bulgarian lung cancer patients surviving for a given period of time in comparison with U.S. populations, the extended survival times achieved by use of the vaccines of our invention assume greatly increased significance.

What is claimed is:

1. Process for preparing antigenic compositions adapted for the treatment of neoplastic diseases in mammals which comprises isolating from the cell nuclei from neoplastic animal tissue (1) a cancer-active single-strand DNA, (2) a cancer-active RNA, and (3) an arginine-rich histone fraction, deaggregating at least one other portion of said cell nuclei by enzymatic treatment with pepsin and isolating from the resulting deaggregated mixture (4) a lysine-rich histone fraction and thereafter recombining fractions (1), (2), and (4) in the presence of streptomycin-cysteine, and combining the product thereof with fraction (3) whereby said four components are reformed by selective recombination/hybridization into antigenic compositions, the components of which have properties and contain amounts of constituents relative to each other in the following ranges:
   A. Single-strand DNA—Molecular weight, $0.5 \times 10^6$ to about $1.5 \times 10^6$
   B. RNA sedimentation constant—4S to 8S
   C. Lysine rich histone Fraction A-1 (LRF):
      Molecular weight: 12,000 to 14,000
      Lysine to arginine mole ratio: 0.5:1 to 4:1
      DNA to LRF weight ratio: 0.5:1 to 4:1
   D. Arginine rich histone fraction (ARF):
      Molecular weight: 10,500 to 13,000
      Lysine to arginine mole ratio 0.3:1 to 0.7:1
      RNA to ARF weight ratio: 0.8:1 to 3.5:1
   E. LRF to ARF weight ratio: 3:1 to 1:4
   F. DNA to RNA weight ratio: 0.3:1 to 3:1

2. The process of claim 1 in which said fractions (2) and (4) are complexed in the presence of streptomycin-cysteine to give a fraction (7), said fraction (7) is hybridized with fraction (1) to give a fraction (6) and said fraction (6) is complexed with fraction (3) to give said antigenic compositions.

3. The process of claim 1 in which said cancer-active single-strand DNA is isolated from repressed single-strand DNA by hybridization of said repressed single-strand DNA with RNA from normal thymus gland.

4. The process of claim 1 in which said RNA is hybridized with denatured DNA from normal thymus gland thereby segregating the non-hybridized cancer-active RNA genome.

5. Process for selection and preparation of fractions (1) and (2) of the antigenic compositions prepared according to the process of claim 1, which comprises identifying the total cancer genome present in a mammalian tumor by the steps of (1) hybridizing denatured DNA from said mammalian tumor with d-DNA from normal calf thymus gland, (2) isolating from step (1) the non-hybridized single-strand DNA from said mammalian tumor whereby there is obtained a cancer-active single-strand DNA, (3) hybridizing RNA from said mammalian tumor with RNA from normal calf thymus gland, (4) isolating from step (3) the non-hybridized RNA of said mammalian tumor whereby there is obtained a cancer-active RNA and whereby the sum of the products isolated from steps 2 and 4 constitute the total cancer genome present in said mammalian tumor and (5) preparing said antigenic compositions from cancer active single-strand DNA and cancer active RNA obtained from animal tumors in which the cancer active single-strand DNA is present in said composition in an amount less than the said total cancer genome in said mammalian tumor.

6. The antigenic composition prepared by the process of claim 1.

7. Antigenic compositions prepared according to the process of claim 1 and adapted for the treatment of neoplastic diseases in mammals, said compositions containing s-DNA, RNA, lysine rich histones and arginine rich histones isolated from cell nuclei of donor animal tumors in which the ratio of active cancer single-strand DNA to cancer active RNA in the animal tumor is present in about the same ratio of the cancer active single strand DNA to the cancer active RNA in said mammals.

8. Antigenic nucleoproteide compositions for use in therapeutic vaccine for the treatment of RNA induced tumors in mammalian hosts which compositions are prepared according to the process of claim 1 by hybridization of cancer-active s-DNA$_c{}^a$, RNA$_c{}^a$, a lysine-rich histone fraction and an arginine rich histone fraction isolated from cancer cell nuclei of donor animals in which the percent hybridization of cancer-active RNA from the donor animal tumor with the RNA from the host mammalian tumor approximates the percent hybridization of cancer-active RNA from the host mammalian tumor with the d-DNA from the host mammalian tumor.

9. Antigenic nucleoproteide compositions for use in therapeutic vaccines for the treatment of DNA induced tumors in mammalian hosts which compositions are prepared according to the process of claim 1 by hybridization of cancer-active s-DNA$_c{}^a$, RNA$_c{}^a$, a lysine-rich histone fraction and an arginine rich histone fraction isolated from cancer cell nuclei of donor animals in which the percent hybridization of d-DNA from the donor animal tumor with the d-DNA from the host mammalian tumor approximates the percent hybridization of cancer-active RNA from the host mammalian tumor with the d-DNA from the host mammalian tumor.

10. Method for treatment of mammals suffering from neoplasms which comprises administering to said mammals therapeutically active antigenic compositions obtained by isolating from separate portions of cell nuclei from neoplastic animal tissue (1) a cancer-active single-strand DNA, (2) a cancer-active RNA, and (3) an arginine-rich histone fraction, deaggregating at least one other portion of said cell nuclei by enzymatic treatment with pepsin and isolating from the resulting deaggregated mixture (4) a lysine-rich histone fraction and thereafter recombining fractions (1), (2), and (4) in the presence of streptomycin-cysteine, and combining the product thereof with fraction (3) whereby said four components are reformed into said antigenic compositions for administration, the components of said antigenic compositions having properties of constituents relative to each other in the following ranges:

A. Single-strand DNA—Molecular weight, $0.5 \times 10^6$ to about $1.5 \times 10^6$
B. RNA sedimentation constant—4S to 8S
C. Lysine rich histone Fraction A-1 (LRF):
  Molecular weight: 12,000 to 14,000
  Lysine to arginine mole ratio: 4:1 to 6:1
  DNA to LRF weight ratio: 0.5:1 to 4:1
D. Arginine rich histone fraction (ARF):
  Molecular weight: 10,500 to 13,000
  Lysine to arginine mole ratio 0.3:1 to 0.7:1
  RNA to ARF weight ratio: 0.8:1 to 3.5:1
E. LRF to ARF weight ratio: 3:1 to 1:4
F. DNA to RNA weight ratio: 0.3:1 to 3:1.

11. The method of claim 10 adapted for treatment of RNA dominant, virus-induced neoplasms in which the therapeutically active antigenic compositions have a weight ratio of single-stranded DNA to RNA of from about 1:2.5 to about 1:5.

12. The method of claim 10 adapted for treatment of DNA dominant neoplasms in which the therapeutically active antigenic compositions have a weight ratio of single-strand DNA to RNA of from about 1:0.2 to about 1:0.6.

13. The method of claim 10 adapted for treatment of RNA dominant, virus-induced neoplasms in which the therapeutically active compositions have a weight ratio of arginine-rich histone to single-strand DNA of at least more than about 4:1.

14. The method of claim 10 adapted for treatment of DNA dominant neoplasms in which the therapeutically active compositions have a weight ratio of arginine-rich histone to single-strand DNA of less than about 2:1.

* * * * *